(12) United States Patent
Pu et al.

(10) Patent No.: US 11,617,043 B2
(45) Date of Patent: Mar. 28, 2023

(54) EEG-ASSISTED BEAMFORMER, BEAMFORMING METHOD AND EAR-WORN HEARING SYSTEM

(71) Applicant: Starkey Laboratories, Inc., Eden Prairie, MN (US)

(72) Inventors: Wenqiang Pu, Guangdong (CN); Jinjun Xiao, Chanhassen, MN (US); Tao Zhang, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 17/265,931

(22) PCT Filed: Aug. 7, 2019

(86) PCT No.: PCT/CN2019/099594
§ 371 (c)(1),
(2) Date: Feb. 4, 2021

(87) PCT Pub. No.: WO2020/029998
PCT Pub. Date: Feb. 13, 2020

(65) Prior Publication Data
US 2021/0306765 A1 Sep. 30, 2021

(30) Foreign Application Priority Data
Aug. 8, 2018 (CN) .......................... 2018108961749

(51) Int. Cl.
*H04R 25/00* (2006.01)
*A61B 5/369* (2021.01)
*A61B 5/00* (2006.01)

(52) U.S. Cl.
CPC ............. *H04R 25/40* (2013.01); *A61B 5/369* (2021.01); *A61B 5/7257* (2013.01);
(Continued)

(58) Field of Classification Search
CPC .... H04R 25/40; H04R 25/505; H04R 25/604; H04R 25/405; H04R 25/00; H04R 2225/43; A61B 5/369; A61B 5/7257
See application file for complete search history.

(56) References Cited

U.S. PATENT DOCUMENTS

| 943,277 A | 12/1909 | Silliman |
| 9,516,430 B2 | 12/2016 | Jensen et al. |

(Continued)

FOREIGN PATENT DOCUMENTS

| CN | 103716744 | 4/2014 |
| CN | 103873999 | 6/2014 |

(Continued)

OTHER PUBLICATIONS

International Search Report and Written Opinion for PCT Application No. PCT/CN2019/099594 dated Oct. 28, 2019, 11 pages.
(Continued)

*Primary Examiner* — Tuan D Nguyen
(74) *Attorney, Agent, or Firm* — Mueting Raasch Group

(57) ABSTRACT

Disclosed is a multi-mode beam former, comprising a device for receiving a multi-mode input signal, and a device for constructing an optimization model and solving the optimization model to obtain a beam-forming weight coefficient for performing linear or non-linear combination on the multi-mode input signal. The optimization model comprises an optimization formula for obtaining the beam-forming weight coefficient. The optimization formula comprises: establishing an association between at least one electroencephalogram signal and a beam forming output, and optimizing the association to construct the beam-forming weight coefficient associated with the at least one electroencephalogram signal.

24 Claims, 7 Drawing Sheets

(52) U.S. Cl.
CPC ......... *H04R 25/505* (2013.01); *H04R 25/604* (2013.01); *H04R 2225/43* (2013.01)

(56) References Cited

U.S. PATENT DOCUMENTS

| | | | |
|---|---|---|---|
| 9,560,458 | B2 | 1/2017 | Lunner et al. |
| 9,700,261 | B2 * | 7/2017 | Lunner ................ H04R 25/554 |
| 10,362,414 | B2 | 7/2019 | Lunner et al. |
| 2006/0094974 | A1 | 5/2006 | Cain |
| 2017/0048626 | A1 * | 2/2017 | Jensen ................ H04R 25/405 |

FOREIGN PATENT DOCUMENTS

| | | |
|---|---|---|
| CN | 104980865 | 10/2015 |
| CN | 105451147 | 3/2016 |
| CN | 107049305 | 8/2017 |
| CN | 107864440 | 3/2018 |
| EP | 3185590 | 6/2017 |

OTHER PUBLICATIONS

Das et al., "EEG-based attention-driven speech enhancement for noisy speech mixtures using n-fold multi-channel wiener filters", in 2017 25th European Signal Processing Conference (EUSIPCO), pp. 1660-1664, Aug. 2017.

Van Eyndhoven et al., "EEG-informed attended talker extraction from recorded speech mixtures with application in neuro-steered hearing prostheses", IEEE Transactions on Biomedical Engineering, 64 (5): 1045-1056, May 2017.

Office Action issued in China for Application No. 201810896174.9 dated Mar. 2, 2022 (12 pages). English translation included.

Biesmans W. et al., "Auditory-Inspired Speech Envelope Extraction Methods for Improved EEG-Based Auditory Attention Detection in a Cocktail Party Scenario", IEEE Transactions on Neural Systems and Rehabilitation Engineering, vol. 25, No. 5, May 2017, pp. 402-412.

Pu, Wenqiang et al., "A Joint Auditory Attention Decoding and Adaptive Binaural Beamforming Algorithm for Hearing Devices", ICASSP 2019—2019 IEEE International Conference on Acoustics, Speech and Signal Processing (ICASSP), IEEE, May 12, 2019, pp. 311-315.

Pu, Wenqiang et al,"An Optimization Model for Electroencephalography-Assisted Bionaural Beamforming", The Journal of the Acoustical Society of America, vol. 143, No. 3, Mar. 1, 2018, p. 1744.

* cited by examiner

EEG-ASSISTED BEAMFORMER, BEAMFORMING METHOD AND EAR-WORN HEARING SYSTEM

TECHNICAL FIELD

The present invention relates to the field of hearing aid technology, specifically to an electroencephalogram-assisted multi-mode beam former and beam forming method used in an ear-mounted hearing system as well as an ear-mounted hearing system comprising the beam former.

BACKGROUND ART

The ear-mounted hearing system is used to help the people suffering from hearing loss by delivering amplified sound to their auditory canals. The damage of the cochlear outer hair cells of the patients results in loss of frequency resolution of the patients' hearing. As this situation develops, it is difficult for the patients to distinguish between speech and environmental noise. Simple amplification cannot solve this problem. Therefore, it is necessary to help such patients discern speech in a noisy environment. Typically, a beam former is used in an ear-mounted hearing system to distinguish speech from noise, in order to help the patients understand speech in a noisy environment.

On the one hand, application of the spatially diverse binaural beam forming technology (provided by a microphone array) in the hearing system is a prior art which can significantly improve user's semantic comprehension of a target talker in a noisy environment with a plurality of talkers. However, two types of widely used beam formers, Multi-channel Wiener Filter (MWF) beam former and Minimum Variance Distortionless Response (MVDR) beam former, require prior information about the target talker, that is, conventional signal processing methods are used to extract the spatial prior information about the talker. Specifically, the MWF beam former needs Voice Activity Detection (VAD) for attended talkers, while the MVDR beam former needs to identify acoustic transfer functions (ATF) of the attended talkers. In practical applications, it is not easy to accurately obtain such spatial prior information from a noisy environment with a plurality of talkers.

On the other hand, the mechanism by which a human brain identifies and tracks a single talker in a noisy environment with a plurality of talkers has been an active research topic in recent decades. In recent years, substantial progress has been made in users' electroencephalograms (EEG), which extract auditory attention (AA) of the user in an environment with a plurality of talkers. For example, S. Van Eyndhoven, T. Francart and A. Bertrand, EEG-informed attended talker extraction from recorded speech mixtures with application in neuro-steered hearing prostheses, IEEE Transactions on Biomedical Engineering, 64 (5): 1045-1056, May 2017 and N. Das, S. Van Eyndhoven, T. Francart and A. Bertrand, EEG-based attention-driven speech enhancement for noisy speech mixtures using n-fold multi-channel wiener filters, in 2017 25$^{th}$ European Signal Processing Conference (EUSIPCO), pages 1660-1664, August 2017 (the above documents are incorporated herein by reference and are for all purposes) have disclosed beam forming methods of AA decoding based on EEG assistance. These methods obtain AA of the users directly from EEG signals, but they all implement beam forming in a stepwise manner, that is, the first step is to extract (decode) AA through the user's EEG signals, and the second step is to implement beam forming or reduce noise based on the decoded AA.

Due to the stepwise implementation process, these methods have the following two disadvantages:

Sensitivity to wrong attention decoding: Since EEG signals reflect the complex activities of human brains, decoded AA may not always be correct. Once AA is decoded incorrectly, the real target talker will be suppressed in the beam forming stage, which is a very bad situation for practical application.

Additional source separation process: In the AA decoding step, in order to obtain the envelope information of every speech source, it is necessary to extract the information of each speech source from the mixed input speech signals received from the microphone, which arouses an additional demand for blind source separation and needs to be implemented by an additional and complex signal processing method.

SUMMARY OF THE INVENTION

Therefore, in order to overcome the above defects, the present application is dedicated to integrating AA decoding and beam forming into an optimization model and allocating user's attention preferences for different speech sources in the form of AA preferences. Specifically, by establishing an inherent association between EEG-assisted AA decoding and binaural beam forming from the perspective of signal processing, a joint algorithm for AA decoding and adaptive binaural beam forming in an ear-mounted hearing system is proposed. This method can effectively use the AA information contained in EEG signals, avoids the problem of sensitivity in the case of incorrect AA decoding and does not need an additional blind source separation process.

The beam former conceived in the present invention is named EEG-assisted binaural beam former. Iterative algorithms with low complexity (i.e., the well-known Gradient Projection Method (GPM) and Alternating Direction Method of Multipliers (ADMM)) are used to solve the proposed formula. The iterative algorithms provide an effective beam former implementation manner that can be implemented in an actual ear-mounted hearing system.

According to an embodiment of the present invention, a beam former is disclosed, comprising: a device for receiving at least one electroencephalogram (EEG) signal and a plurality of input signals from a plurality of speech sources; and a device for constructing an optimization model and solving the optimization model to obtain a beam-forming weight coefficient for performing linear or non-linear combination on the plurality of input signals, wherein the optimization model comprises an optimization formula for obtaining the beam-forming weight coefficient, and the optimization formula comprises establishing an association between the at least one electroencephalogram signal and a beam forming output, and optimizing the association to construct a beam-forming weight coefficient associated with at least one electroencephalogram signal.

According to an alternative embodiment of the present invention, a beam forming method for a beam former is disclosed, comprising the following steps: receiving at least one electroencephalogram (EEG) signal and a plurality of input signals from a plurality of speech sources; and constructing an optimization model and solving the optimization model to obtain a beam-forming weight coefficient for performing linear or non-linear combination on the plurality of input signals, wherein the optimization model comprises an optimization formula for obtaining the beam-forming weight coefficient, and the optimization formula comprises establishing an association between the at least one electroencephalogram signal and a beam forming output, and optimizing the association to construct a beam-forming weight coefficient associated with at least one electroencephalogram signal.

According to an alternative embodiment of the present invention, an ear-mounted hearing system is disclosed, comprising: a microphone, which is configured to receive a plurality of input signals from a plurality of speech sources; an electroencephalogram signal receiving interface, which is configured to receive information from one or more electroencephalogram electrodes and perform linear or non-linear transformation on the electroencephalogram information to form at least one electroencephalogram (EEG) signal; a beam former, which receives the plurality of input signals and the at least one EEG signal and outputs a beam-forming weight coefficient; a synthesis module, which linearly or non-linearly synthesizes the plurality of input signals and the beam-forming weight coefficient to form a beam forming output; and a loudspeaker, which is configured to convert the beam forming output into an output sound, wherein the beam former is a beam former according to the present invention.

According to a further embodiment of the present invention, a computer-readable medium including instructions is disclosed. When being executed by a processor, the instructions can cause the processor to implement the beam forming method according to the present invention.

Compared with the prior art method of incorporating EEG signals into beam forming in a stepwise manner (i.e., first decoding AA, and then performing beam forming), the present invention integrates AA decoding and beam forming into an optimization model, thereby effectively using the AA information contained in the EEG signals, avoiding the problem of sensitivity in the case of incorrect AA decoding and not needing an additional blind source separation process.

DETAILED DESCRIPTION

The present disclosure will now be described in more detail with reference to the following embodiments. It should be noted that the following description of some embodiments herein is presented only for schematic and illustrative purposes and not intended to be exhaustive or be limited to the disclosed precise forms.

In the mathematical formulas shown in the present application, boldfaced lowercase letters represent vectors and boldfaced uppercase letters represent matrices; H is a sign of conjugate transpose, and T is a sign of transpose; the set of all n-dimensional complex vectors is expressed as $C^n$; and $X_i \in C$ is the i-th element of $X \in C^n$. The following specific implementation manners of the present application cite the subject matter in the accompanying drawings in the form of examples. The drawings of the description of the present application show the specific aspects and embodiments of the subject matter of the present application that can be implemented. These embodiments are fully described so that those skilled in the art may implement the subject matter of the present application. The citation of "an or one" embodiment or "various" embodiments of the present disclosure is not necessarily specific to the same embodiments, and such citation is expected to cover more than embodiment. The following implementation manners are illustrative and not adopted for the purpose of limitation.

Hereinafter, mathematical formulas for describing a beam former according to embodiments of the present application will be presented. The beam former according to embodiments of the present application is designed to establish an inherent association between EEG-assisted AA decoding and binaural beam forming from the perspective of signal processing, improve the speeches of attended talkers in a noisy environment with a plurality of talkers and reduce other impacts. In order to effectively use the AA information contained in EEG signals, in the beam former according to embodiments of the present application, the inherent association between EEG-assisted AA decoding and binaural beam forming implements the electroencephalogram-assisted beam former by balancing the following two aspects: (I) Allocation of AA preferences under the constraint of speech fidelity; and (II) Noise reduction and interference suppression.

Figure 1:
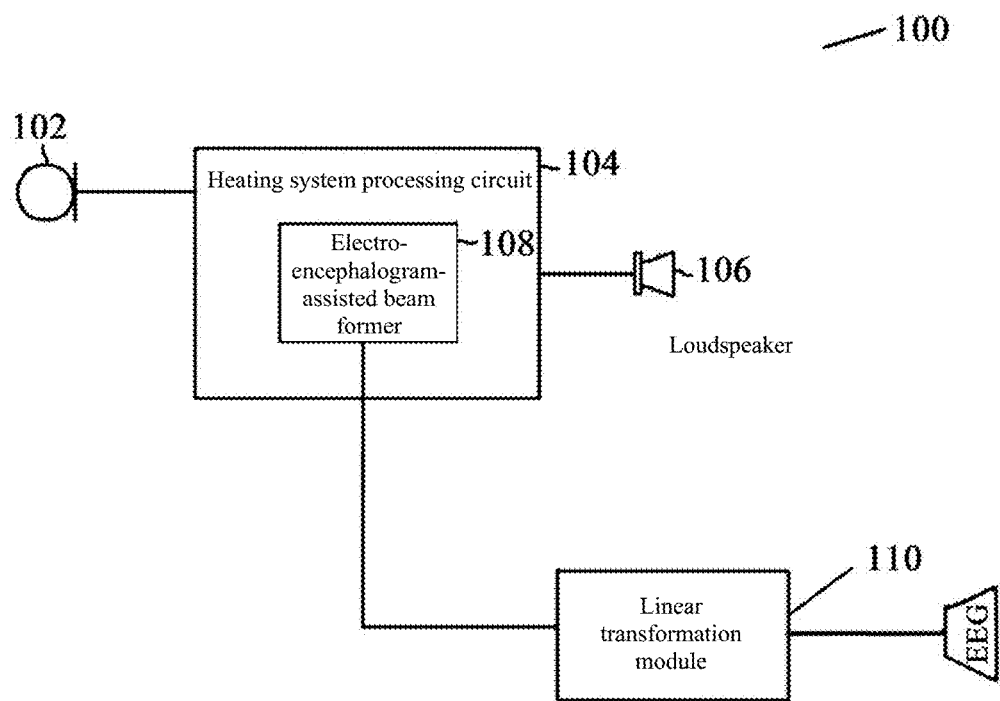
FIG. 1 is a block diagram of an exemplary embodiment of an ear-mounted hearing system according to the present invention.

FIG. 1 is a block diagram of an exemplary embodiment of an ear-mounted hearing system 100 according to the present invention. The hearing system 100 comprises an electroencephalogram-assisted beam former 108 and a linear transformation module 110. The hearing system 100 further comprises a microphone 102, a hearing system processing circuit 104 and a loudspeaker 106. The electroencephalogram-assisted beam former 108 may be arranged in a hearing system processing circuit 104 and may also be arranged in separation of the hearing system processing circuit 104. In the description below, the electroencephalogram-assisted beam former 108 arranged in the hearing system processing circuit 104 is taken as an example. In an embodiment, there are K speech sources, also called talkers, in an environment with a plurality of talkers, including target talker and background talkers (who simulate background noise). When one of the target talkers talks with the user of the ear-mounted hearing system, the target talker is called an attended talker, while other target talkers are considered interferences (also called unattended talkers). The microphone 102 shown in FIG. 1 represents M microphones, all receiving an input sound and generating an electrical signal representing the input sound. The processing circuit 104 processes (one or more) microphone signals to generate an output signal. The loudspeaker 106 uses the output signal to generate an output sound including the speech. In various embodiments, an input sound may comprise various components, a speech and a noise interference, as well as a sound fed back by the loudspeaker 106 via a sound feedback path. The processing circuit 104 comprises an adaptive filter to reduce noise and sound feedback. In the embodiment shown, the adaptive filter comprises an electroencephalogram-assisted beam former 108. Further, FIG. 1 also shows a linear transformation module 110, which is configured to receive EEG signals from the head of the user of the hearing system through a sensor on the head of the user and perform linear transformation on the received EEG signals to obtain an optimized linear transformation coefficient. The linear transformation coefficient reconstructs the envelope of speech sources according to the EEG signals to obtain a reconstructed envelope of the speech sources, and the linear transformation module 110 is further configured to transfer the reconstructed envelope to the electroencephalogram-assisted beam former 108. In various embodiments, when the hearing system 100 is implemented, the processing circuit 104 receives microphone signals, and the electroencephalogram-assisted beam former 108 uses the microphone signals from the hearing system and the reconstructed envelope to provide adaptive binaural beam forming.

Figure 2A:
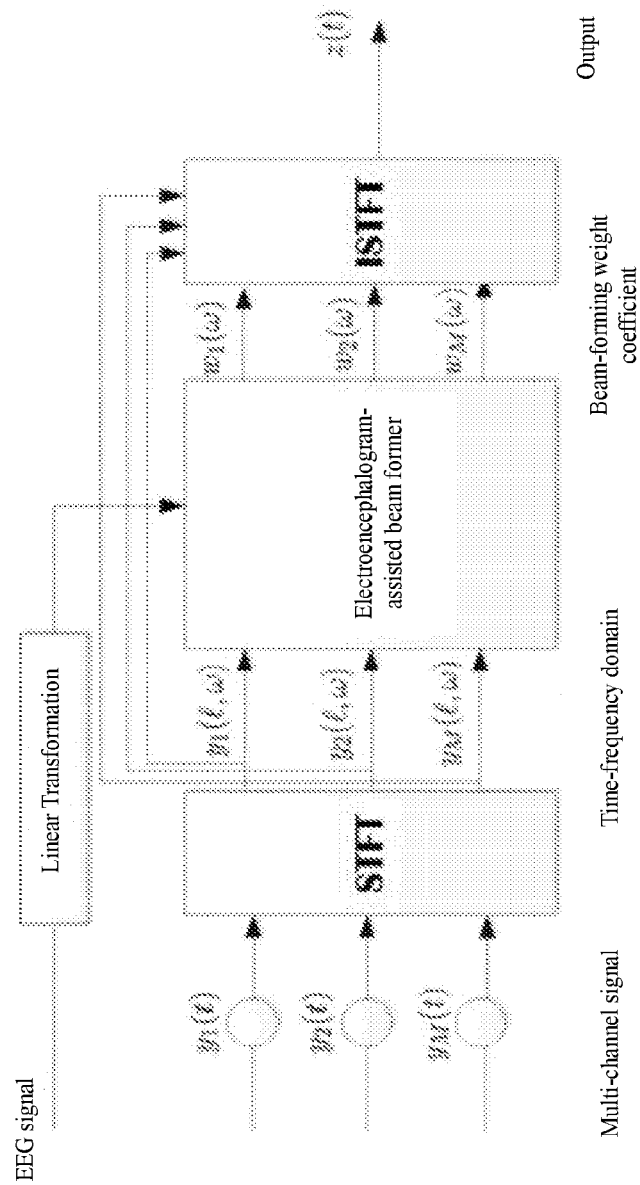
FIG. 2A is a schematic view of the working principle of an electroencephalogram-assisted beam former according to the present invention.

FIG. 2A is a schematic view of the working principle of an electroencephalogram-assisted beam former of the present disclosure. In an embodiment of the present invention, as shown in FIG. 1, a microphone signal received by the electroencephalogram-assisted beam former 108 as an input speech signal of the electroencephalogram-assisted beam former 108 can be expressed as follows in a time-frequency domain through short-time Fourier transform (STFT):

$$y(\ell, \omega) = \sum_{k=1}^{K} h_k(\omega) s_k(\ell, \omega) + n(\ell, \omega), \tag{1}$$

where y(l, ω)∈$C^M$ represents a microphone signal at frame l (each frame corresponds to N input signal samples in the time domain) and band ω (ω=1, 2, ..., Ω); $h_k(\omega) \in C^M$ is an acoustic transfer function (ATF) of the k-th speech source, and $s_k(l, \omega) \in C$ is a corresponding input speech signal under the time-frequency domain; and n(l, ω)∈$C^M$ represents background noise. FIG. 2A shows microphone signals $y_1(t)$, $y_2(t)$ and $y_M(t)$ and corresponding signals $y_1(l, \omega)$, $y_2(l, \omega)$ and $y_M(l, \omega)$ in the time-frequency domain in the form of examples only.

In an embodiment of the present invention, the electroencephalogram-assisted beam former 108 linearly combines input speech signals to generate output signals at each ear, as shown in FIG. 2A. Specifically, let $\omega_L(\omega) \in C^M$ and $\omega_R(\omega) \in C^M$ respectively represent beam formers used in the left ear and the right ear at band w. The output signals at the left loudspeaker and the right loudspeaker are:

$$z_L(l,\omega)=w_L{}^H(\omega)y(l,\omega), z_R(l,\omega)=w_R{}^H(\omega)y(l,\omega)$$

Through inverse STFT (ISTFT) on $\{z_L(l, \omega)\}_{l,\omega}$ and $\{z_R(l, \omega)\}_{l,\omega}$, time-domain representation output by beam forming can be synthesized. To simplify the notation, L and R will be omitted in the rest of this document. By simply specifying the reference microphone on the left or right side of the hearing system, the design standard of the present invention can be applied to the left or right ear.

In an embodiment of the present invention, the electroencephalogram-assisted beam former 108 is configured to comprise a device for constructing an optimization model and solving the optimization model, which establishes an inherent association between EEG-assisted AA decoding and binaural beam forming from the perspective of signal processing based on a regression model of AA decoding, and balances the following two aspects: (I) allocation of AA preferences under the constraint of speech fidelity; and (II) noise reduction and interference suppression to obtain a beam-forming weight coefficient that linearly combines a plurality of input speech signals, wherein the optimization model includes an optimization formula, which is used for suppressing the interference in a plurality of input speech signals and obtaining a beam-forming weight coefficient. In various embodiments, the processing circuit 104 is configured to further solve the optimization formula by using iterative algorithms with low complexity, so that the output signals of the electroencephalogram-assisted beam former 108 conform to the standard for allocation of AA preferences under the constraint of speech fidelity and noise reduction in the output signals.

In an embodiment of the present disclosure, the linear transformation module 110 is configured to obtain an optimized linear transformation coefficient, thereby reconstructing the envelope of the speech sources to obtain a reconstructed envelope of the speech sources. In other words, in an embodiment of the present disclosure, electroencephalogram signals are transformed to the envelope of the speech signals of the speech sources by linear transformation, and then a beam former design is performed by solving an optimization model. Further, using the electroencephalogram signals in the beam former design includes without limitation the linear transformation method disclosed by the embodiment of the present invention, and also includes other methods, such as non-linear transformation, or a method using a neural network. Specifically, let $e_i(t) \in R$ be an EEG signal of EEG channel i (i=1, 2, ..., C) when the user is at time t (t=1, 2, ...), suppose talker 1 is an attended talker (a target talker talking with the user of the hearing system) and his envelope is $s_1(t)$, and let $s_a(t)$ represent an envelope of speech signals of attended speech sources corresponding to input speech signals in the time domain. In terms of mean square error, an optimization model formula is provided:

$$\min_{\{g_i(\tau)\}} E\left\{\left|\left[\sum_{i=1}^{C}\sum_{\tau=\tau_1}^{\tau_2} g_i(\tau)e_i(t+\tau)\right]-s_a(t)\right|^2\right\} + \lambda h(\{g_i(\tau)\}). \tag{2}$$

In Formula 2, $g_i(\tau)$ is a linear regression coefficient corresponding to an EEG signal with a delay τ, and E is an expected operator. Regular function $$h\{g_i^*(\tau)\} \triangleq \left[\sum_{i=1}^{C}\sum_{\tau=\tau_1}^{\tau_2-1}|g_i(\tau)-g_i(\tau+1)|^2 + \sum_{i=1}^{C-1}|g_i(\tau_2)-g_{i+1}(\tau_1)|^2\right]$$

specifies the time smoothing preference of the linear regression coefficient $g_i(\tau)$, and means that $g_i(\tau)-g_i(\tau+1)$ cannot be too large. Further, λ≥0 is a corresponding regular parameter, and $\{e_i(t)\}_{i=1}^{C}$ is an EEG signal, and has different delays τ=$\tau_1$, $\tau_1$+1, ..., $\tau_2$. Optimization formula 2 is a convex quadratic formula having the closed-form solutions given in the methods disclosed in W. Biesmans, N. Das, T. Francart, and A. Bertrand, Auditory-inspired speech envelope extraction methods for improved eeg-based auditory attention detection in a cocktail party scenario, IEEE Transactions on Neural Systems and Rehabilitation Engineering, 25 (5):

402-412, May 2017 (the above documents are incorporated herein by reference and are for all purposes), and will not be described herein. In this way, an optimized linear transformation coefficient $\{g_i^*(\tau)\}$ is obtained, where $$\{g_i^*(\tau)\} = \arg\min_{\{g_i(\tau)\}} \mathbb{E}\left\{\left\|\left[\sum_{i=1}^{C}\sum_{\tau=\tau_i}^{\tau_2} g_i(\tau)e_i(t+\tau)\right] - s_a(t)\right\|^2\right\} + \lambda h(\{g_i(\tau)\}),$$

this linear transformation coefficient, reconstructs the envelope $s_a(t)$ of the attended speech sources according to the EEG signals.

Based on the obtained optimized linear transformation coefficient $\{g_i^*(\tau)\}$, the envelope of the attended speech sources can be reconstructed into $\hat{s}_\alpha(t) = \Sigma_i \Sigma_\tau g_i^*(\tau) e_i(t+\tau)$ according to the EEG signals.

Next, an inherent association between EEG signals and beam forming signals will be provided. Intuitively, the physical meaning of the optimization formula 2 is that the reconstructed envelope $\hat{s}_a(t)$ should have a strong correlation to the envelope $s_1(t)$ of the attended talker. On the other hand, the beam forming output in fact is a mixture of different kinds of input signals received by the microphone and specified by the beam former. In the case of appropriate provisions of the beam former, $s_1(t)$ can be a main component at the beam forming output. Therefore, a natural and direct way to use EEG signals to design a beam former is to maximize the Pearson correlation between the reconstructed envelope $\hat{s}_a(t)$ of the speech sources and the envelope of the beam forming output.

For this purpose, firstly a mathematical formula for the envelope of the beam forming output under the time domain is given. In an embodiment of the present disclosure, the electroencephalogram-assisted beam former 108 is configured to obtain an envelope of a beam forming output. Specifically, from the perspective of signal processing, sampling is expressed each time as a function of the beam former. It is assumed that beam forming outputs correspond to time sampling indexes t, t+1, ..., t+N−1. If z(t), z(t+1), ..., z(t+N−1) express beam forming outputs under the time domain, then the envelope in fact is an absolute value of corresponding $\tilde{z}(t), \tilde{z}(t+1), \ldots, \tilde{z}(t+N-1)$ in an analytical signal form and can be expressed as follows through discrete Fourier transform (DFT) according to the beam-forming weight coefficient $\{w(\omega)\}_\omega$.

$$\begin{bmatrix} \tilde{z}(t) \\ \tilde{z}(t+1) \\ \vdots \\ \tilde{z}(t+N-1) \end{bmatrix} = D_W F D_H \begin{bmatrix} w(1)^H y(\ell, 1) \\ w(2)^H y(\ell, 2) \\ \vdots \\ w(\Omega)^H y(\ell, \Omega) \end{bmatrix} \quad (3)$$

In Formula 3, $D_H \in \mathbb{R}^{\Omega \times \Omega}$ is a diagonal matrix for forming analytical signals, $F \in \mathbb{C}^{\Omega \times \Omega}$ is the inverse of a DFT matrix, while $D_W \in \mathbb{R}^{\Omega \times \Omega}$ is a diagonal matrix for compensating a synthesis window used in short-time Fourier transform (STFT) that is used to express a plurality of input signals. In order to simplify symbols, Formula 3 is abbreviated as:

$$\tilde{z}(t+n) = w^H u_{\ell,n}, n=0,1,\ldots,N-1, \quad (4)$$

where $w = [w(1)^H, w(2)^H, \ldots, w(\Omega)^H]^H \in \mathbb{C}^{M\Omega}$ is a beam-forming weight coefficient to be solved, and $u_{\ell,n} \in \mathbb{C}^{M\Omega}$ is determined by $\{y(l, \omega)\}_\omega$ and the coefficients in matrices $D_W$, F and $D_H$. Through Formulas 3 and 4, the envelope of the beam forming output is expressed as:

$$|\tilde{z}(t+n)| = |w^H u_{\ell,n}|, n=0,1,\ldots,N-1. \quad (5)$$

Further, in an embodiment of the present disclosure, the electroencephalogram-assisted beam former 108 is configured to obtain a Pearson correlation between the reconstructed envelope $\hat{s}_a(t)$, which is transferred by the linear transformation module 110, and the envelope $|\tilde{z}(t)|$ of the beam forming output. Specifically, for given time slots $t=t_1, t_1+1, \ldots, t_2$, the Pearson correlation coefficient between the envelope $\hat{s}_a(t)$ of the corresponding speech sources and the envelope $|\tilde{z}(t)|$ of the beam forming output is expressed as:

$$\kappa(\{w(\omega)\}) = \frac{\sum_{t=t_1}^{t_2} \psi_{s,t} \psi_{z,t}(\{w(\omega)\})}{\sqrt{\frac{1}{t_2-t_1+1}\sum_{t=t_1}^{t_2} \psi_{s,t}^2} \sqrt{\frac{1}{t_2-t_1+1}\sum_{t=t_1}^{t_2} \psi_{z,t}(\{w(\omega)\})^2}}, \quad (6)$$

where $\psi_{s,t} = \hat{s}_a(t) - \frac{1}{t_s-t_1+1}\sum_{t'=t_1}^{t_2} \hat{s}_a(t')$ and $$\psi_{z,t}(\{w(\omega)\}) = |\tilde{z}(t)| - \frac{1}{t_2-t_1+1}\sum_{t'=t_1}^{t_2} |\tilde{z}(t')|.$$

It should be noted that Formula 6 supposes that the reconstructed envelope $\hat{s}_a(t)$ of the speech sources and the envelope $|\tilde{z}(t)|$ of the beam forming output are synchronized at the same sampling rate. In fact, the reconstructed envelope $\hat{s}_a(t)$ of the speech sources has a sampling rate that is the same as that of EEG signals (i.e., tens of or hundreds of Hz), while the envelope $|\tilde{z}(t)|$ of the beam forming output corresponds to an audio sampling rate (i.e., 16 kHz). An additional synchronizing process is needed, but this process does not change Formula 6, in other words, $\tilde{z}(t)$ is re-sampled from Formula 4 according to the ratio between the sampling rates of the input speech signals and the EEG signals.

Next, by maximizing the Pearson correlation coefficient $\kappa(\{w(\omega)\})$, the AA information contained in the EEG signals is extracted to design a beam former. However, the actual design of a biaural beam former also needs some other non-negligible considerations, including but not limited to speech distortion, noise reduction and interference suppression. Therefore, the optimization formula for the electroencephalogram-assisted beam former of the present invention combines the Pearson correlation coefficient $\kappa(\{w(\omega)\})$ with the following two factors:

(1) Allocation of AA preferences under the constraint of speech fidelity: From the perspective of signal processing, designing a beam former $\{w(\omega)\}_\omega$ only by maximizing the Pearson correlation coefficient $\kappa(\{w(\omega)\})$ may result in uncontrollable speech distortion of every speech source. Any change of space response at $w(\omega)^H h_k(\omega)$ between different bands is permitted. Therefore, in order to control speech distortion, a group of robust equality constraints $\omega(\omega)^H h_k(\omega) = \alpha_k, \forall \omega$ is applied to ensure that all space responses of the k-th speech source on all bands share a common real value $\alpha_k$. This equality constraint means that the component of the input speech signals of the k-th speech source at the beam forming output is scaled up or down by $\alpha_k$ only and does not have any frequency distortion. Under the above considerations, allocation of AA preferences is formulated as:

$$\max_{\{w(\omega)\},\alpha} \kappa(\{w(\omega)\}) \text{ s.t. } w(\omega)^H h_k(w) = \alpha_k, \forall k, \omega, \quad (7a)$$

$$1^T \alpha = 1, \alpha_k k \geq 0, \forall k. \quad (7b)$$

In Formula 7, $\kappa(\{w(\omega)\})$ represents the Pearson correlation coefficient defined in Formula 6. It is a smoothed non-convex function about beam-forming weight coefficient $\{w(\omega)\}_\omega$ on all bands. The additional variable $\alpha=[\alpha_1, \alpha_2, \ldots, \alpha_K]^T$ and the constraint (7a) ensure that the input speech signals of K speech sources at the beam forming output are linearly combined by $\alpha$, and Formula 7b indicates that the sum of the elements in vector $\alpha=[\alpha_1, \alpha_2, \ldots, \alpha_K]^T$ is 1. In this way, a in fact expresses AA preferences in K speech sources.

(2) Noise reduction and interference suppression: In addition to adjusting AA, it is also considered to reduce the energy of background noise in the form of minimum variance:

$$\min_{w(\omega)} \mathbb{E}\left[|w(\omega)^H n(\omega)|^2\right] \equiv \min_{w(\omega)} w(\omega)^H R_n(\omega) w(\omega), \tag{8}$$

where $R_n(\omega) \triangleq \mathbb{E}[n(\omega)n(\omega)]$ is a correlation matrix of background noise.

Further, in an embodiment of the present disclosure, the electroencephalogram-assisted beam former 108 is configured to obtain an optimization formula of the electroencephalogram-assisted beam former 108 according to the above factors. Specifically, by combining Formulas 7 and 8, an optimization formula used in the electroencephalogram-assisted beam former 108 according to the present invention can be obtained:

$$\min_{\{w(\omega)\},\alpha} \sum_{\omega=1}^{\Omega} w(\omega)^H R_n(\omega) w(\omega) - \mu\kappa(\{w(\omega)\}) - \gamma\|\alpha\|^2 \tag{9}$$

s.t. $w(\omega)^H h_k(\omega) = \alpha_k, \forall k, \omega,$ $1^T \alpha = 1, \alpha_k \geq 0, \forall k.$ In Formula 9, the additional regular term $-\gamma\|\alpha\|^2$ is a regular term of the optimization formula, where $\|\cdot\|^2$ represents a Euclidean norm of vector $\alpha=[\alpha_1, \alpha_2, \ldots, \alpha_K]T$, and specifies sparse preferences of AA. This term allocates a $\alpha_k$ toward 1 and allocates other $\alpha_k$ toward 0. $\mu>0$ and $\gamma\geq 0$ are preset parameters and are used to balance denoising, allocate attention preferences and control the sparseness of attention preferences.

In various embodiments, the processing circuit 104 is configured to solve the optimization formula by using iterative algorithms with low complexity (i.e., well-known GPM and ADMM). In an embodiment of the present invention, due to non-linear functions $-\mu\kappa(\{w(\omega)\})$ and $-\gamma\|\alpha\|^2$, Formula 9 is a non-convex formula. As the constraint prefers a favorable form, i.e., a separable linear constrain about beam former $\{w(\omega)\}_\omega$ on band $\omega$ in Formula 7a, GPM is used for solving. By adopting this separable attribute, implementation manners effective in calculation are admitted. In the case of the appropriate step size rule (i.e., the Armijo rule is used in the experiment), GPM utilizes guaranteed convergence (see D. P. Bertsekas, Nonlinear programming, Athena Scientific Belmont, Proposition 2.3 in 1999) to solve Formula 9. As the main calculation work of GPM in solving Formula 9 is to use ADMM to solve a formula of a projection on the polyhedron defined by Formulas (7a) and (7b), a parallel implementation manner of the original update of the closed form beam former $\{w(\omega)\}\omega$ is caused. The solving algorithm follows the standard update process of GPM and ADMM algorithms.

Below, a specific process of solving the optimization formula used in the electroencephalogram-assisted beam former 108 according to the present invention will be introduced. Specifically, the objective function in Formula 9 is expressed as:

$$f(\{w(\omega)\},\alpha) \triangleq \sum_{\omega=1}^{\Omega} w(\omega)^H R_n(\omega) w(\omega) - \mu\kappa(\{w(\omega)\}) - \gamma\|\alpha\|^2,$$

Let $\nabla f = [\nabla f_1, \nabla f_2, \ldots, \nabla f_\Omega, \nabla f_\alpha]^T$ It is a gradient of the objective function $f(\{w(\omega)\}, \alpha)$, where $\nabla f_\omega$ (or $\nabla f_\alpha$) represents a gradient component about $w(\omega)$ (or $\alpha$). GPM iteratively updates $x \triangleq (\{w(\omega)\}, \alpha)$ into:

$$\bar{x} = [x^t - s\nabla f^t]^+ \tag{10a}$$

$$x^{t+1} = x^t + \lambda^t(\bar{x} - x^t), \tag{10b}$$

where t is an iteration index, $\nabla f^t$ is a gradient of objective function $f(\{w(\omega)\}, \alpha)$ at $x^t$, $[\ ]^+$ represents projection operation of equality constraints (7b) and (7a), s is a predetermined positive scalar (constant), and $\lambda^t$ is a step size determined according to the Armijo rule. The main calculation process of the foregoing GPM update is the projection operation in Formula (10a). Next, an ADMM algorithm will be derived for Formula (10a), which is an iterative algorithm with low complexity and accepts parallel implementation manners on bands.

The projection operation in Formula (10a) is same as a convex optimization equation (omit iteration index t)

$$\min_{\{w(\omega)\},\alpha} \sum_{\omega=1}^{\Omega} \|w(\omega) - s\nabla f_\omega\|^2 + \|\alpha - s\nabla f_\alpha\|^2 \tag{11a}$$

s.t. $w(\omega)^H h_k(\omega) = \alpha_k, \forall k, \omega,$ \tag{11b}

$1^T \alpha = 1, \alpha_k \geq 0, \forall k.$ \tag{11c}

The augmented Lagrangian function for Equation 11 is:

$$L_\rho(\{w(\omega)\}, \alpha, \{\zeta_{k,\omega}\}, \eta) = \sum_{\omega=1}^{\Omega} \|w(\omega) - s\nabla f_\omega\|^2 + \|\alpha - s\nabla f_\alpha\|^2 + \eta(\alpha - 1) +$$

$$\frac{\rho}{2}\|1^T\alpha - 1\|^2 + \sum_{k=1}^{K}\sum_{\omega=1}^{\Omega} \zeta_{k,\omega}\left[w(\omega)^H h_k(\omega) - \alpha_k\right] + \frac{\rho}{2}\|w(\omega)^H h_k(\omega) - \alpha_k\|^2,$$

where $\zeta_{k,w}$ and $\eta$ are Lagrangian factors, which are correlated to equality constraints (7a) and (7b) respectively; $\rho>0$ is a predefined parameter for the ADMM algorithm. As $L_\rho$ for $\{w(\omega)\}$ on band w is separable, the ADMM algorithm iteratively updates $(\{w(\omega)\}, \alpha, \{\zeta_{k,w}\}, \eta)$ into:

$$w^{l+1}(\omega') = \arg\min_{w(\omega')} L_\rho\left(w(\omega'), \{w^l(\omega)\}_{\omega \neq \omega'}, \alpha^l, \{\zeta^l_{k,\omega}\}, \eta^l\right), \forall \omega' \tag{12a}$$

$$\alpha = \arg\min_{\alpha \geq 0} L_\rho\left(\{\omega^{l+1}(\omega)\}, \alpha, \{\zeta^l_{k,\omega}\}, \eta^l\right) \tag{12b}$$

$$\zeta^{l+1}_{k,\omega} = \zeta^l_{k,\omega} + \rho\left[\omega^{l+1}(\omega)^H h_k(\omega) - \alpha^{l+1}_k\right], \forall k, \omega \tag{12c}$$

$$\eta^{l+1} = \eta^l + \rho(1^T\alpha - 1) \tag{12d}$$

where l is an iteration index.

It should be noted that Formula (12a) is a simple unconstrained convex quadratic formula and has closed-form solutions (iterative algorithms with low complexity are used). Formula (12b) is a convex quadratic formula with a non-negative constraint $\alpha \geq 0$ and can be solved easily. All ADMM updates use iterative algorithms with low complexity, and Formulas (12a) and (12c) can be further implemented in parallel in actual application to raise calculation efficiency.

Figure 2B:
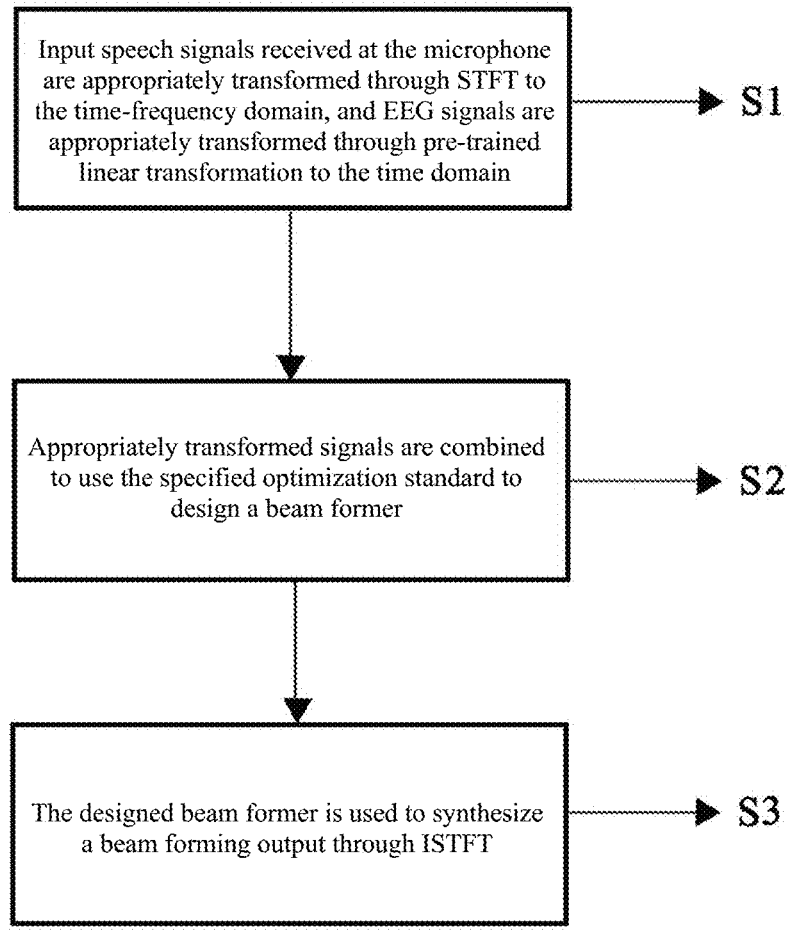
FIG. 2B is a schematic flowchart of a beam forming method implemented through the electroencephalogram-assisted beam former shown in FIG. 2A.

In an embodiment of the present invention, an inherent association between EEG signals and beam forming signals is established from the perspective of signal processing, and AA decoding and beam forming are integrated in a single optimization model (Formula 9). FIG. 2A is a schematic view of the working principle of an electroencephalogram-assisted beam former according to the present invention. FIG. 2B is a flowchart corresponding to FIG. 2A, and shows a flowchart of an electroencephalogram-assisted beam forming method consisting of three steps according to the present disclosure. As shown in FIGS. 2A and 2B, this embodiment shows three channels of speech signals only in the form of an example, but the present invention is not limited to this. In the first step S1, input speech signals $y_1(t)$, $y_2(t)$ and $y_M(t)$ received at the microphone are appropriately transformed through STFT to signals $y_1(l, \omega)$, $y_2(l, \omega)$ and $y_M(l, \omega)$ in the time-frequency domain, and EEG signals are appropriately transformed through pre-trained linear transformation to the time domain and are input to the electroencephalogram-assisted beam former. In the second step S2, appropriately transformed signals (including transformed input speech signals and transformed EEG signals) are combined to use the above optimization standard to design a beam former, for the purpose of enhancing the speech of the attended talker with the AA information contained in the EEG signals to obtain beam-forming weight coefficients $\omega_1(\omega)$, $\omega_2(\omega)$ and $\omega_M(\omega)$. In the last step S3, the beam-forming weight coefficients obtained by the designed electroencephalogram-assisted beam former are used to perform combination on the signals $y_1(l, \omega)$, $y_2(l, \omega)$ and $y_M(l, \omega)$ that have undergone SFTF to synthesize a beam forming output through ISTFT.

Figure 3:
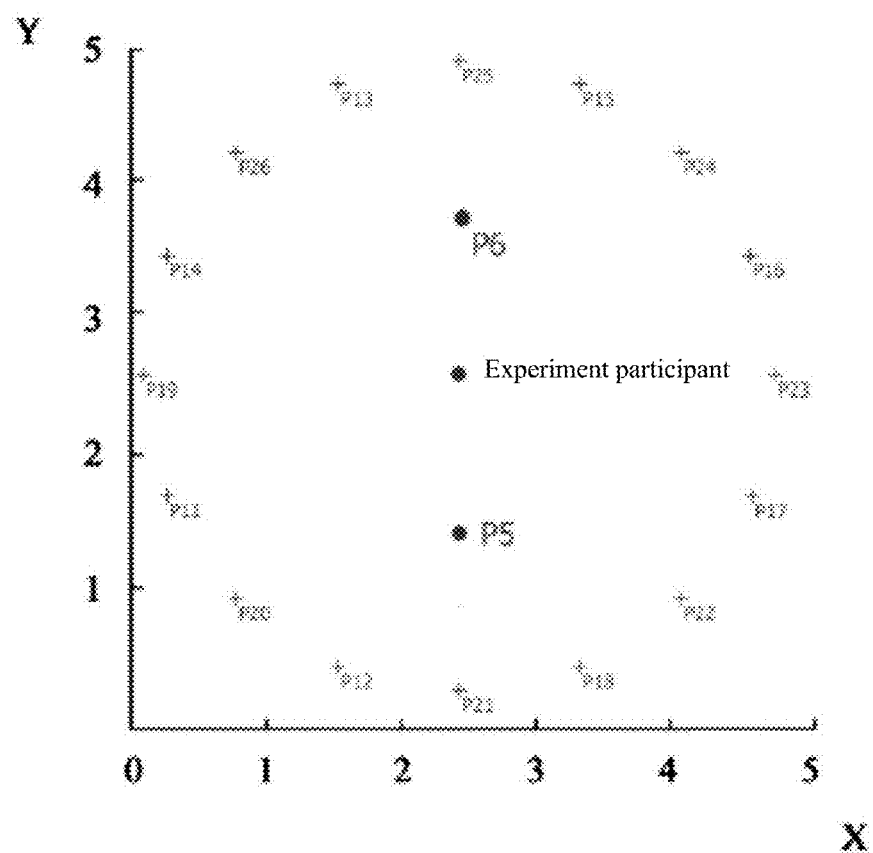
FIG. 3 is a top view of a simulated acoustic environment for comparing the electroencephalogram-assisted beam forming method of the present invention with the source separation (SP)-linearly constrained minimum variance (LCMV) method.

Below, an EEG database will be introduced. Experiment participants are selected from this EEG database to do follow-up experiments to reflect the performance advantages of the beam forming method according to the present invention. FIG. 3 is a top view of a simulated acoustic environment for comparing the electroencephalogram-assisted beam forming method according to an embodiment of the present application with the source separation (SP)-linearly constrained minimum variance (LCMV) method. In the simulated acoustic environment (in the system of rectangular coordinates as shown in FIG. 3, a range of 5 m*5 m on a horizontal plane at a certain height in the room is selected as a part of the room), as shown in FIG. 3, there are 18 speech sources (talkers) in total, and among them, only P5 and P6 are target talkers, while P11 to P26 are all background talkers, which are used for simulating background noise; the experiment participant is in the middle of the room; P5 and P6 are over and under the experiment participant, respectively, and are 1 m from the experiment participant; P11 to P26 are uniformly distributed on the circumference with the experiment participant as the center of the circle and with a radius of 2 m. In other words, the included angle between two adjacent loudspeakers is 22.5°, and P25 is over the experiment participant, as shown in FIG. 3.

In a noisy and echoic environment with a plurality of talkers, EEG signals are collected from four experiment participants with normal hearing. The experiment participants are at the center of the room and talkers are under and over the experiment participants (P5, P6). When the experiment participants are listening to the speech of one of the two talkers, the other one of the two talkers is an interference. The remaining 16 speech sources distributed in the room are used to generate background noise. The same speech volume and intensity are set for the two talkers, and 5 dB higher than those of background noise. In the experiment, a group of ER-3 insert earphones are used to present obtained audio signals to the experiment participants, and the intensity of the audio signals is at a "loud and comfortable" level.

The experiment participants are instructed to complete a binaural hearing task and meanwhile listen to the speech of one of the talkers.

Specifically, in an embodiment of the present invention, some experimental conditions and four experiment participants are selected from the EEG database for evaluation. In an embodiment of the present invention, every experiment participant participating in this experiment is required to focus their attention on talkers P5 and P6 each for 10 minutes. The total time recorded for each experiment participant is 20 minutes. The 20 recorded minutes are divided into 40 non-overlapping time slots with a length of 30 seconds. A cross validation is reserved among these time slots to train and optimize the linear transformation coefficient $\{g_i^*(\tau)\}$ and evaluate beam forming performance. Specifically, for each time slot, by incorporating its corresponding 30 seconds of EEG signals and trained $\{g_i^*(\tau)\}$ into a beam forming process, $\{g_i^*(\tau)\}$ trains all other time slots and the beam forming performance is self-evaluated.

A 64-channel scalp EEG system is used to record the responses of the experiment participants at a sampling frequency of 10 kHz. All recording is completed on the hardware of a brain product.

In this way, an EEG database is established. Below, the beam forming method according to the present invention will be evaluated according to the established EEG database.

Specifically, in an embodiment of the present invention, in order to study the performance differences between the beam forming method according to the present invention and other separable methods (AA decoding and beam forming are typically combined in a separable manner, i.e., a source separation method is used to extract speech signals of AA decoding from talkers, and then beam forming is performed based on decoded AA), and a separable method based on LCMV (linearly constrained minimum variance) beam forming is used as a reference. This method uses two different LCMV beam formers (i.e., linear constraints are used to reserve a speech source and refuse the other speech source) to separate the signals of the two speech sources by comparing the Pearson correlations of the separated signals with regard to the reconstructed envelope $\hat{s}_a(t)$ and then decode AA. The LCMV beam forming output with a larger Pearson correlation is selected as the final beam forming output. For the sake of convenience, this method is used as a source separation (SP)-LCMV method.

Intelligibility-weighted SINR improvement (IW-SINRI) and intelligibility-weighted spectral distortion (IW-SD) are used as performance measurement criteria to evaluate beam forming output signals.

In this experiment, EEG signals and the input signals received at the microphone are resampled at 20 Hz and 16 kHz respectively. In the training stage of linear regression coefficient $g_i(\tau)$, all C=63 EEG channels are used in Formula 2, and the delay of the EEG signals is specified to be 0 to 250 ms for every EEG channel (corresponding to $\tau$=0, 1, . . . , 5 under a sampling rate of 20 Hz). The expectation operation in Formula 2 is replaced with the sample average of the samples recorded in a limited manner, and $\lambda$ in Formula 2 is fixed and is $5*10^{-3}$. In the beam forming evaluation stage, 512-point FFT with 50% overlap is used in STFT (Hanning window).

Figure 4:
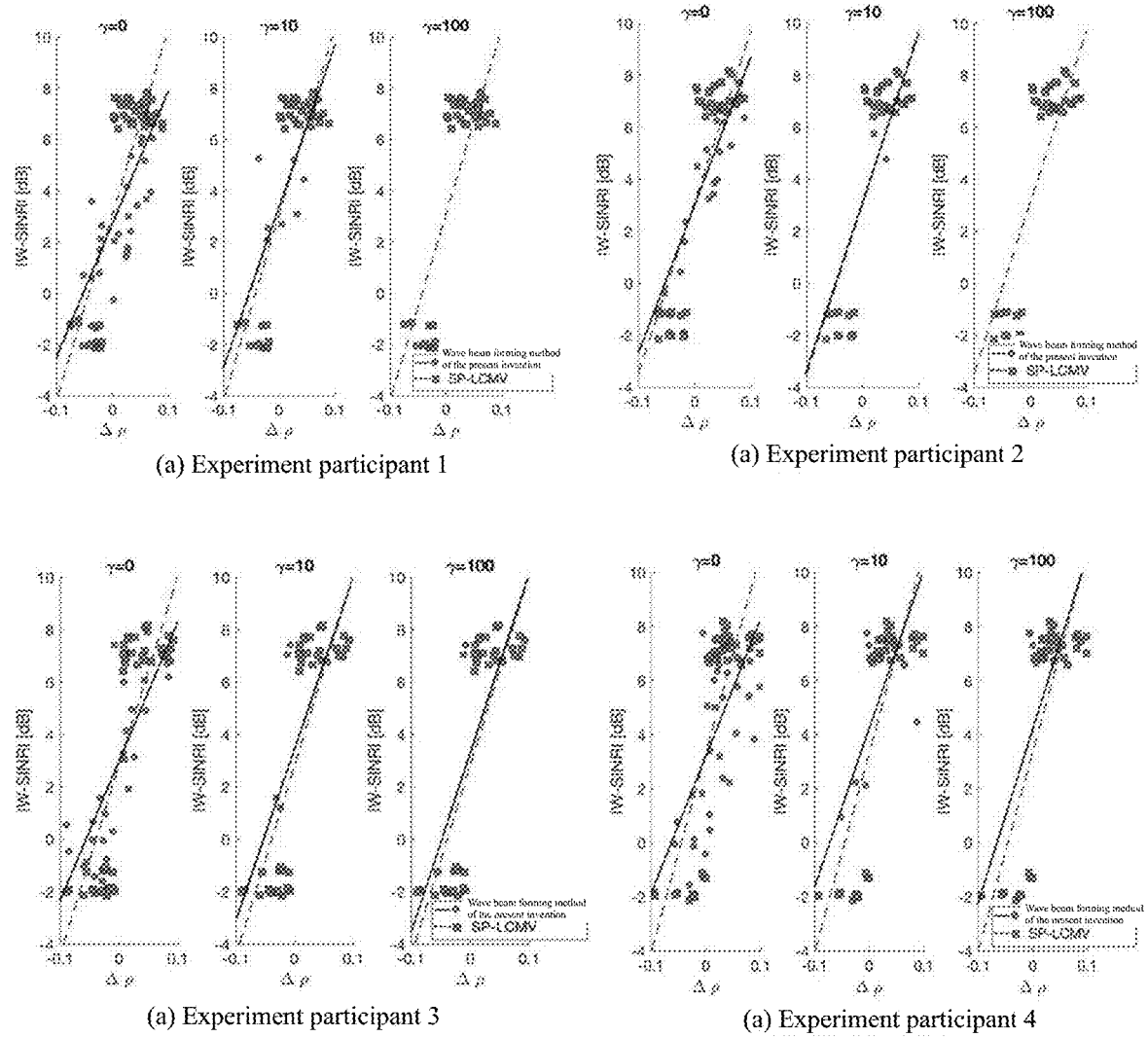
FIG. 4 shows how differences between IW-SINRI and Pearson correlation in the beam forming method of the present invention and the SP-LCMV method are related.

FIG. 4 shows the difference in speech enhancement behavior between the beam forming method of the present invention and the SP-LCMV method in dealing with the uncertainty of AA information, and indicates the relationship of the difference $\Delta\rho=\rho_{att}-\rho_{unatt}$ between IW-SINRI and Pearson correlation, where $\rho_{att}$ ($\rho_{unatt}$) is a Pearson correlation between the reconstructed envelope $\hat{s}_a(t)$ and the input signals of the attended (unattended) signals, and is separated from microphone signals by an appropriate LCMV beam former. In addition, the solid lines and round dots in FIG. 4 represent the data obtained by the beam forming method of the present application, while the dotted lines and square dots represent the data obtained by the SP-LCMV method. Particularly, as shown in FIG. 4, for experiment participant 2, when $\gamma$=10, the solid line and the dotted line obtained by the two methods almost coincide with each other. The AA information contained in the EEG signals is encoded through the obtained optimized linear transformation coefficient $\{g_i^*(\tau)\}$ according to the envelope $\hat{s}_a(t)$. In some aspects, the value of $\Delta\rho$ reflects a confidence in the possibility that the speech sources are attended speech sources. According to FIG. 4, it can be observed that when $\gamma$=0, the IW-SINRI range in the method of the present invention is from −2 dB to 8 dB. This is because the method of the present invention allocates AA preferences of some values ranging from 0 to 1 for attended speech sources. As for the SP-LCMV method, due to the AA decoding process separated by it, IW-SINRI is grouped as about −2 dB or 8 dB. When $\gamma$ is increased to 100, the method of the present invention is in a bipolar form and has a result very similar to the result of the SP-LCMV method. Meaningfully, when $\gamma$=0, an approximately linear correlation between IW-SINRI and $\Delta\rho$ can be observed, which shows a capability of the method of the present invention in capturing the uncertainty of AA information. The larger $\Delta\rho$ is, the higher the confidence in AA of the attended speech sources will be and the higher the achieved IW-SINRI will be.

Figure 5:
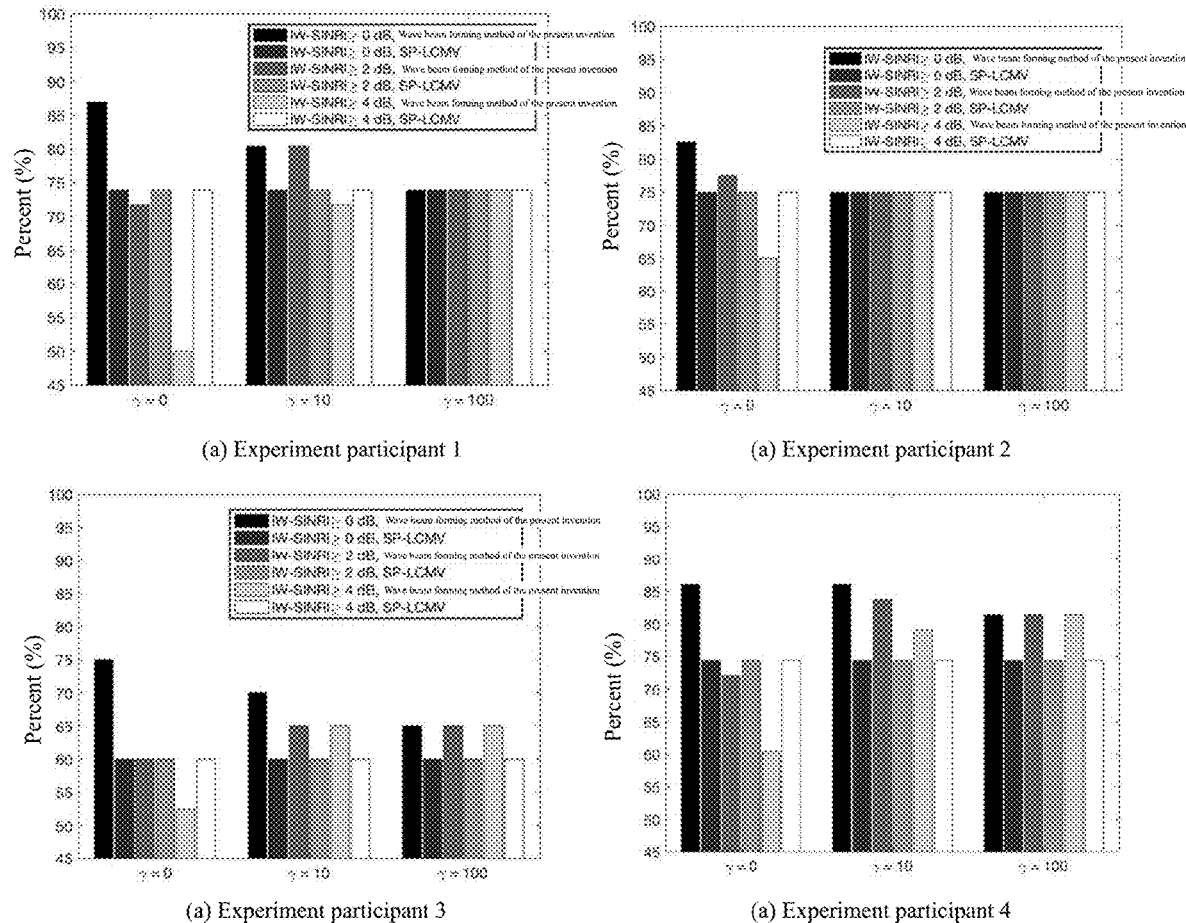
FIG. 5 shows the percentages of IW-SINRI of greater than or equal to 0 dB, 2 dB and 4 dB in the beam forming method of the present invention and the SP-LCMV method.

As the method of the present invention enhances speeches in a gentle manner, in order to quantitatively evaluate its speech enhancement capability, the percentage of a corresponding time slot of IW-SINRI with a certain threshold is used as an evaluation measurement criterion. Specifically, in FIG. 5, the percentages of IW-SINRI of greater than or equal to 0 dB, 2 dB and 4 dB in the method of the present invention and the SP-LCMV method are compared. As shown in the figure, for each $\gamma$ of each experiment participant, the depths of the six bar graphs decrease gradually, and specifically, for example, in terms of (a) experiment participant 1 in FIG. 5, when $\gamma$=0, the depths of the six obtained percentage bar graphs decrease gradually. From left to right, the six bar graphs are: data obtained by the beam forming method of the present application when IW-SINRI is greater than or equal to 0 dB; data obtained by the SP-LCMV method when IW-SINRI is greater than or equal to 0 dB; data obtained by the beam forming method of the present application when IW-SINRI is greater than or equal to 2 dB; data obtained by the SP-LCMV method when IW-SINRI is greater than or equal to 2 dB; data obtained by the beam forming method of the present application when IW-SINRI is greater than or equal to 4 dB; and data obtained by the SP-LCMV method when IW-SINRI is greater than or equal to 4 dB, as shown in the notes in the figure. Similarly, in terms of (a) experiment participant 1 in FIG. 5, the distributions of bar graphs when $\gamma$=10 and when $\gamma$=100 are similar; further, the distributions of bar graphs of other experiment participants in FIG. 5 exhibit a similar trend.

It can be discovered that when $\gamma$=0, the method of the present invention has the largest percentage for IW-SINRI≥0 dB and the smallest percentage for IW-SINRI≥4 dB. It means that when $\gamma$=0, the method of the present invention implements a "safety strategy" for enhanced speech, that is, for the time slots with $\Delta\rho$ of approximately 0, as mainly shown in FIG. 4, each speech source is partially retained at the beam forming output. In another aspect, as $\gamma$ increases, more time slots have an IW-SINRI of greater than 4 dB and the consumption of IW-SINRI in some time slots is lower than 0 dB. Further, $\gamma$=100 shows a result similar to the result of the SP-LCMV method.

Figure 6:
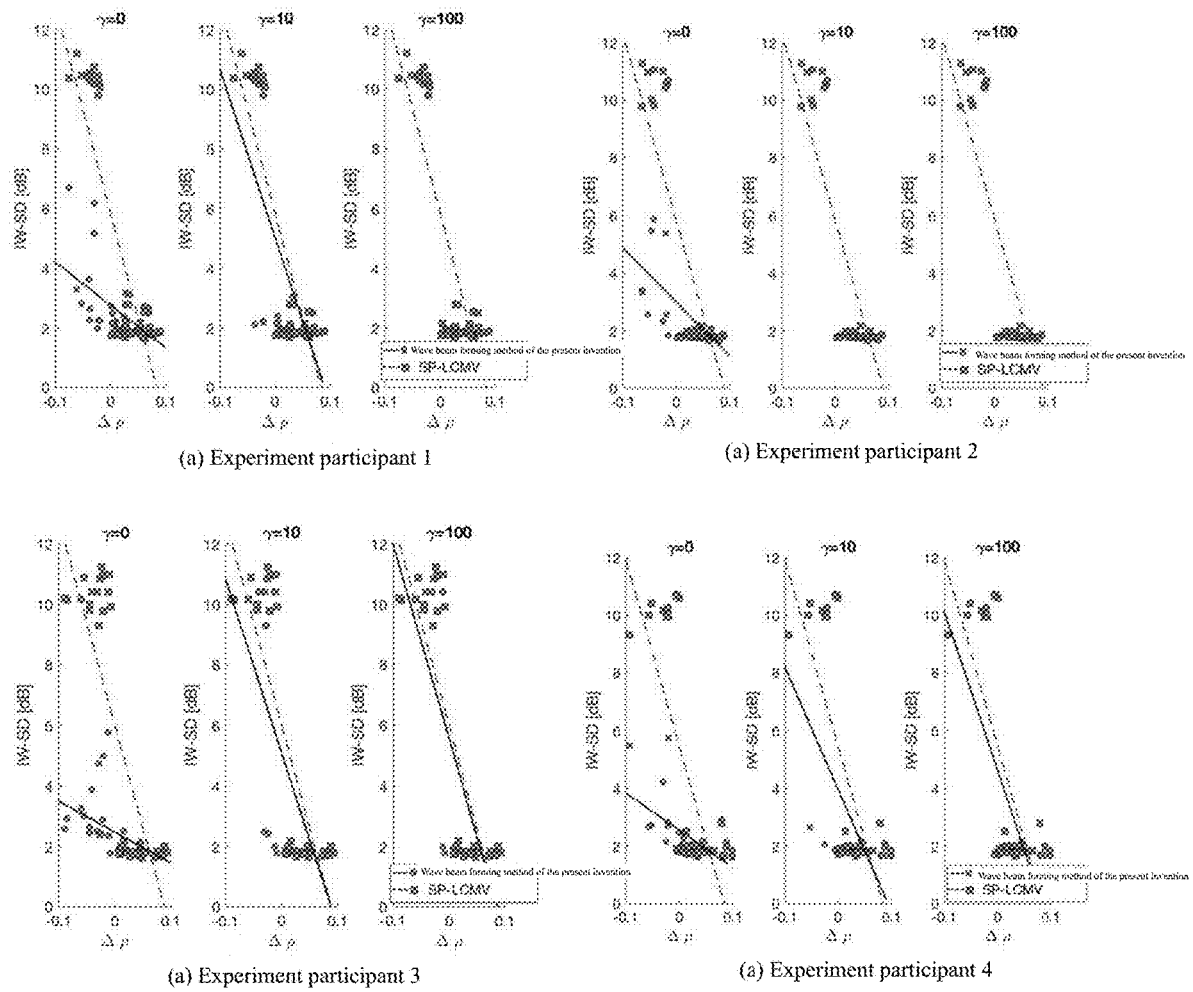
FIG. 6 shows how differences between IW-SD and Pearson correlation in the beam forming method of the present invention and the SP-LCMV method are related.

Further, another important issue of speech enhancement is speech distortion. As the method of the present invention and the SP-LCMV method have linear constraints for each speech source, they have similar IW-SDs, as shown in FIG. 6. FIG. 6 shows how differences between IW-SD and Pearson correlation in the method of the present invention and the SP-LCMV method are related, wherein the solid lines and round dots in FIG. 6 represent the data obtained by the beam forming method of the present application, while the dotted lines and square dots represent the data obtained by the SP-LCMV method. It should be noted that the method of the present invention adjusts $\alpha_k$ in a range from 0 to 1. During calculation of IW-SD, the speech signals at the beam forming output are scaled up or down according to $\alpha_k$. Further, for these two methods, the time slots when the attended speech sources are completely refused (i.e., $w(\omega)^H h(\omega)$=0) are not shown in FIG. 6.

The beam former according to an embodiment of the present application works based on EEG-assisted AA decoding and is designed to establish an inherent association between EEG-assisted AA decoding and binaural beam forming from the perspective of signal processing, improve the speech of attended talkers in a noisy environment with a plurality of talkers and reduce other impacts. In order to effectively use the AA information contained in EEG signals, in the beam former according to embodiments of the present application, the inherent association between EEG-assisted AA decoding and binaural beam forming implements the electroencephalogram-assisted beam former by balancing the following two aspects: (I) allocation of AA preferences under the constraint of speech fidelity; and (II) noise reduction and interference suppression.

It should be understood that the ear-mounted hearing system cited by the present application comprises a processor, which can be a DSP, a microprocessor, a microcontroller or any other digital logic. The signal processing cited by the present application can be implemented using the processor. In various embodiments, the processing circuit 104 can be implemented on such processor. The processing can be completed in a digital domain, an analog domain or a combination thereof. The sub-band processing technology can be used to complete the processing. The frequency domain or time domain method can be used to complete the processing. For convenience, in some examples, block diagrams for performing frequency synthesis, frequency analysis, A/D conversion, amplification, and other types of filtering and processing can be omitted. In various embodiments, the processor is configured to execute the instructions stored in a memory. In various embodiments, the processor executes instructions to implement several signal processing tasks. In such embodiments, the communication between the component and the processor is simulated to implement the signal task, for example, a microphone reception or receiver sound embodiment (i.e., in applications using such sensor). In various embodiments, the block diagrams, circuits or processes proposed herein can be implemented without departing from the scope of the subject matter of the present application.

The subject matter of the present application is presented for use in an ear-mounted hearing system, comprising a hearing aid, including but not limited to behind-the-ear (BTE) aid, in-the-ear (ITE) aid, in-the-canal (ITC) aid, receiver-in-the-canal (RIC) aid or complete-in-the-canal (CIC) aid. It should be understood that a BTE aid may comprise the devices principally behind or above the ear. Such devices may include hearing aids comprising a receiver associated with the electronic part of a BTE device or hearing aids comprising a receiver in the user's canal, including but not limited to a receiver in the canal (RIC) or a receiver in the ear (RITE). The subject matter of the present application can generally be used in a hearing aid, too, for example, an artificial cochlea type hearing device. It should be understood that other hearing devices not expressly stated herein can be used with the subject matter of the present application in a combined manner.

Further, the following exemplary embodiments of the present invention are described:

Embodiment 1: A beam former, comprising:
a device for receiving at least one electroencephalogram (EEG) signal and a plurality of input signals from a plurality of speech sources; and
a device for constructing an optimization model and solving the optimization model to obtain a beam-forming weight coefficient for performing linear or non-linear combination on the plurality of input signals;
wherein the optimization model comprises an optimization formula for obtaining the beam-forming weight coefficient, and the optimization formula comprises establishing an association between the at least one electroencephalogram signal and a beam forming output, and optimizing the association to construct a beam-forming weight coefficient associated with at least one electroencephalogram signal.

Embodiment 2: The beam former according to Embodiment 1, wherein establishing an association between the at least one electroencephalogram signal and a beam forming output includes establishing an association between the at least one electroencephalogram signal and a beam forming output by using non-linear transformation or by a method using a neural network.

Embodiment 3: The beam former according to Embodiment 1, wherein establishing an association between the at least one electroencephalogram signal and a beam forming output includes using linear transformation to establish an association between the at least one electroencephalogram signal and a beam forming output.

Embodiment 4: The beam former according to Embodiment 3, wherein the optimization formula comprises a Pearson correlation coefficient:

$$\kappa(\{w(\omega)\}) = \frac{\sum_{t=t_1}^{t_2} \psi_{s,t}\psi_{z,t}(\{w(\omega)\})}{\sqrt{\frac{1}{t_2-t_1+1}\sum_{t=t_1}^{t_2}\psi_{s,t}^2}\sqrt{\frac{1}{t_2-t_1+1}\sum_{t=t_1}^{t_2}\psi_{z,t}(\{w(\omega)\})^2}}, \quad (6)$$

-continued $$\text{where } \psi_{s,t} = \hat{s}_a(t) - \frac{1}{t_s-t_1+1}\sum_{t'=t_1}^{t_2}\hat{s}_a(t') \text{ and}$$

$$\psi_{z,t}(\{w(\omega)\}) = |\tilde{z}(t)| - \frac{1}{t_2-t_1+1}\sum_{t'=t_1}^{t_2}|\tilde{z}(t')|,$$

and where $\hat{s}_a(t)$ is an envelope of speech signals of attended speech sources, which is reconstructed by the at least one EEG signal; z(t) represents a beam forming output; $\tilde{z}(t)$ is an analytical signal corresponding to the beam forming output; $|\tilde{z}(t)|$ is an envelope of the beam forming output and is an absolute value of the analytical signal $\tilde{z}(t)$; $\kappa(\{w(\omega)\})$ represents the Pearson correlation coefficient between the reconstructed envelope $\hat{s}_a(t)$ of speech signals of attended speech sources and the envelope $|\tilde{z}(t)|$ of the beam forming output for the given time slots $t=t_1, t_1+1, \ldots, t_2$; $\{w(\omega)\}_\omega$ is a beam-forming weight coefficient; $\omega$ ($\omega=1, 2, \ldots, \Omega$) represents a band.

Embodiment 5: The beam former according to Embodiment 4, further comprising a device for receiving a reconstructed envelope of speech signals of attended speech sources, wherein based on an optimized linear transformation coefficient $\{g_i^*(\tau)\}$, according to the at least one EEG signal, the reconstructed envelope of $\hat{s}_a(t)=\Sigma_i\Sigma_\tau g_i^*(\tau)e_i(t+\tau)$ of speech signals of attended speech sources is obtained, and the reconstructed envelope of speech signals of attended speech sources is transferred to the device for receiving a reconstructed envelope of speech signals of attended speech sources, wherein by solving the following formula, the optimized linear transformation coefficient $\{g_i^*(\tau)\}$ is obtained:

$$\min_{\{g_i(\tau)\}} E\left\{\left|\left[\sum_{i=1}^{C}\sum_{\tau=\tau_1}^{\tau_2} g_i(\tau)e_i(t+\tau)\right] - s_a(t)\right|^2\right\} + \lambda h(\{g_i(\tau)\}). \quad (2)$$

where $e_i(t) \in R$ is an EEG signal corresponding to EEG channel i (i=1, 2, ..., C) in the at least one EEG signal at time t (t=1, 2, ...) and r is a time delay; $S_\alpha(t)$ represents an envelope of speech signals of the attended speech sources corresponding to the plurality of input signals; $g_i(\tau)$ is a linear regression coefficient of the EEG signal corresponding to the EEG channel i with a delay $\tau$, and E is an expected operator; regular function $$h(\{g_i(\tau)\}) \triangleq \left[\sum_{i=1}^{C}\sum_{\tau=\tau_1}^{\tau_2-1}|g_i(\tau)-g_i(\tau+1)|^2 + \sum_{i=1}^{C-1}|g_i(\tau_2)-g_{i+1}(\tau_1)|^2\right]$$

delimits the time smoothness of the linear regression coefficient $g_i(\tau)$; and $\lambda \geq 0$ is a corresponding regular parameter.

Embodiment 6: The beam former according to Embodiment 5, wherein the analytical signal is expressed as follows through discrete Fourier transform (DFT) according to the beam-forming weight coefficient $\{w(\omega)\}_\omega$:

$$\begin{bmatrix} \tilde{z}(t) \\ \tilde{z}(t+1) \\ \vdots \\ \tilde{z}(t+N-1) \end{bmatrix} = D_W F D_H \begin{bmatrix} w(1)^H y(\ell, 1) \\ w(2)^H y(\ell, 2) \\ \vdots \\ w(\Omega)^H y(\ell, \Omega) \end{bmatrix} \quad (3)$$

where $D_H \in R^{\Omega \times \Omega}$ is a diagonal matrix for forming the analytical signals and $F \in C^{\Omega \times \Omega}$ is the inverse of the DFT matrix; $y(l, \omega) \in C^M$ represents the plurality of input signals at frame l and band $\omega$ ($\omega=1, 2, \ldots, \Omega$), frame l corresponds to N sampling time points t, t+1, ..., t+N-1, while $D_W \in R^{\Omega \times \Omega}$ is a diagonal matrix for compensating a synthesis window used in short-time Fourier transform (STFT) that is used to express the plurality of input signals, and the analytical signal is further equivalently expressed as:

$$\tilde{z}(t+n) = w^H u_{\ell, n}, n=0, 1, \ldots, N-1, \quad (4)$$

where $w = [w(1)^H, \omega(2)^H, \ldots, w(\Omega)^H]^H \in \mathbb{C}^{M\Omega}$ is the beam-forming weight coefficient, and $u_{l,n} \in \mathbb{C}^{M\Omega}$ is determined by $\{y(l\omega)\}_\omega$ and the coefficients in matrices $D_W$, F and $D_H$, and through the analytical signals, the envelope $|\tilde{z}(t)|$ of the beam forming output is expressed as:

$$|\tilde{z}(t+n)| = |w^H u_{\ell, n}|, n=0, 1, \ldots, N-1. \quad (5)$$

Embodiment 7: The beam former according to Embodiment 6, wherein the sampling rate of the envelope $|\tilde{z}(t)|$ of the beam forming output corresponds to the audio sampling rate of the plurality of input signals.

Embodiment 8: The beam former according to Embodiment 6, wherein optimizing the association to construct a beam-forming weight coefficient associated with at least one electroencephalogram signal includes maximizing the Pearson correlation coefficient $\kappa(\{w(\omega)\})$ to extract the AA information contained in the at least one EEG signal.

Embodiment 9: The beam former according to Embodiment 8, wherein in the process of maximizing the Pearson correlation coefficient $\kappa(\{w(\omega)\})$, robust equality constraint $w(\omega)^H h_k(\omega) = \alpha_k$, $\forall \omega$ is applied to control speech distortion, where $\alpha = [\alpha_1, \alpha_2, \ldots, \alpha_K]^T$ is an additional variable, which represents AA preference in the plurality of speech sources; $h_k(\omega)$ is an acoustic transfer function of the k-th speech source; and K is the number of the plurality of speech sources.

Embodiment 10: The beam former according to Embodiment 9, wherein the optimization formula becomes:

$$\min_{\{w(\omega)\}, \alpha} \sum_{\omega=1}^{\Omega} w(\omega)^H R_n(\omega) w(\omega) - \mu \kappa(\{w(\omega)\}) - \gamma \|\alpha\|^2 \quad (9)$$

s.t. $w(\omega)^H h_k(\omega) = \alpha_k, \forall k, \omega,$ $1^T \alpha = 1, \alpha_k \geq 0, \forall k.$ where $R_n(\omega) \triangleq \mathbb{E}[n(\omega)n(\omega)]$ is a correlation matrix of background noise; $-\gamma \|\alpha\|^2$ is a regular term of the optimization formula, where $\|\cdot\|^2$ represents a Euclidean norm of the additional variable $\alpha = [\alpha_1, \alpha_2, \ldots, \alpha_K]^T$; $\mu > $ and $\gamma \geq 0$ are preset parameters and are used to balance denoising, allocate attention preferences and control the sparseness of attention preferences, and $1^T \alpha = 1, \alpha_k \geq 0, \forall k$ indicates that the sum of the elements in the additional variable is 1.

Embodiment 11: The beam former according to Embodiment 10, wherein the optimization model is solved by the gradient projection method (GPM) and the alternating direction method of multipliers (ADMM), including the following steps:

(a) The objective function in the optimization formula is expressed as:

$$f(\{w(\omega)\}, \alpha) \triangleq \sum_{\omega=1}^{\Omega} w(\omega)^H R_n(\omega) w(\omega) - \mu \kappa(\{w(\omega)\}) - \gamma \|\alpha\|^2$$

and let $\nabla f = [\nabla f_1, \nabla f_2, \ldots, \nabla f_\Omega, \nabla f_\alpha]^T$ represent the gradient of the optimization formula, where $\nabla f_\omega$ represents a gradient component about $w(\omega)$; and $\nabla f_\alpha$ represents a gradient component about $\alpha$;

(b) The GPM iteratively updates $x \triangleq (\{w(\omega)\}, \alpha)$ to:

$$\bar{x} = [x^t - s \nabla f^t]^+ \quad (10a)$$

$$x^{t+1} = x^t + \lambda^t (\bar{x} - x^t), \quad (10b)$$

where t is an iteration index, $\nabla f^t$ is a gradient of the objective function at $x^t$, $[\cap]^+$ represents the projection operation of equality constraints $w(\omega)^H h_k(\omega) = \alpha_k$, $\forall \omega$ and $x^T \alpha = 1, \alpha_k \geq 0, \forall_k$, s is a constant, and $\lambda^t$ is a step size determined according to the Armijo rule;

(c) The projection operation in Formula (10a) is same as the following convex optimization equation:

$$\min_{\{w(\omega)\}, \alpha} \sum_{\omega=1}^{\Omega} \|w(\omega) - s \nabla f_\omega\|^2 + \|\alpha - s \nabla f_\alpha\|^2 \quad (11a)$$

s.t. $w(\omega)^H h_k(\omega) = \alpha_k, \forall k, \omega,$ (11b)

$1^T \alpha = 1, \alpha_k \geq 0, \forall k.$ (11c)

The augmented Lagrangian function for Equations 11a, 11b and 11c is:

$$L_\rho(\{w(\omega)\}, \alpha, \{\zeta_{k,\omega}\}, \eta) = \sum_{\omega=1}^{\Omega} \|w(\omega) - s \nabla f_\omega\|^2 + \|\alpha - s \nabla f_\alpha\|^2 + \eta(\alpha - 1) +$$

$$\frac{\rho}{2} \|1^T \alpha - 1\|^2 + \sum_{k=1}^{K} \sum_{\omega=1}^{\Omega} \zeta_{k,\omega} [w(\omega)^H h_k(\omega) - \alpha_k] + \frac{\rho}{2} \|w(\omega)^H h_k(\omega) - \alpha_k\|^2,$$

where $\zeta_{k,w}$ and $\eta$ are Lagrangian factors, which are correlated to the equality constraints respectively; $\rho > 0$ is a predefined parameter for the ADMM algorithm, (d) The ADMM algorithm iteratively updates ($\{w(\omega)\}, \alpha, \{\zeta_{k,\omega}\}$ η) into:

$$w^{l+1}(\omega') = \arg\min_{w(\omega')} L_\rho(w(\omega'), \{w^l(\omega)\}_{\omega \neq \omega'}, \alpha^l, \{\zeta_{k,\omega}^l\}, \eta^l), \forall \omega' \quad (12a)$$

$$\alpha = \arg\min_{\alpha \geq 0} L_\rho(\{\omega^{l+1}(\omega)\}, \alpha, \{\zeta_{k,\omega}^l\}, \eta^l) \quad (12b)$$

$$\zeta_{k,\omega}^{l+1} = \zeta_{k,\omega}^l + \rho[\omega^{l+1}(\omega)^H h_k(\omega) - \alpha_k^{l+1}], \forall k, \omega \quad (12c)$$

$$\eta^{l+1} = \eta^l + \rho(1^T \alpha - 1) \quad (12d)$$

where l is an iteration index; and
(e) A result of Formula 12 is obtained.

Embodiment 12: A beam forming method for beam former, comprising the following steps:

receiving at least one electroencephalogram (EEG) signal and a plurality of input signals from a plurality of speech sources; and constructing an optimization model and solving the optimization model to obtain a beam-forming weight coefficient for performing linear or non-linear combination on the plurality of input signals;

wherein the optimization model comprises an optimization formula for obtaining the beam-forming weight coefficient, and the optimization formula comprises establishing an association between the at least one electroencephalogram signal and a beam forming output, and optimizing the association to construct a beam-forming weight coefficient associated with at least one electroencephalogram signal.

Embodiment 13: The beam forming method according to Embodiment 12, wherein establishing an association between the at least one electroencephalogram signal and a beam forming output includes establishing an association between the at least one electroencephalogram signal and a beam forming output by using nonlinear transformation or by a method using a neural network.

Embodiment 14: The beam forming method according to Embodiment 12, wherein establishing an association between the at least one electroencephalogram signal and a beam forming output includes establishing an association between the at least one electroencephalogram signal and a beam forming output by using linear transformation.

Embodiment 15: The beam forming method according to Embodiment 14, wherein the optimization formula includes a Pearson correlation coefficient:

$$\kappa(\{w(\omega)\}) = \frac{\sum_{t=t_1}^{t_2} \psi_{s,t}\psi_{z,t}(\{w(\omega)\})}{\sqrt{\frac{1}{t_2-t_1+1}\sum_{t=t_1}^{t_2}\psi_{s,t}^2}\sqrt{\frac{1}{t_2-t_1+1}\sum_{t=t_1}^{t_2}\psi_{z,t}(\{w(\omega)\})^2}}, \quad (6)$$

where $$\psi_{s,t} = \hat{s}_a(t) - \frac{1}{t_s-t_1+1}\sum_{t'=t_1}^{t_2}\hat{s}_a(t'),$$

$$\psi_{z,t}(\{w(\omega)\}) = |\tilde{z}(t)| - \frac{1}{t_2-t_1+1}\sum_{t'=t_1}^{t_2}|\tilde{z}(t')|$$

and where $\hat{s}_a(t)$ is an envelope of speech signals of attended speech sources, which is reconstructed by the at least one EEG signal; z(t) represents a beam forming output; $\tilde{z}(t)$ is an analytical signal corresponding to the beam forming output; $|\tilde{z}(t)|$ is an envelope of the beam forming output and is an absolute value of the analytical signal $\tilde{z}(t)$; $\kappa(\{w(\omega)\})$ represents a Pearson correlation coefficient between the reconstructed envelope $\hat{s}_a(t)$ of speech signals of speech sources and the envelope $|\tilde{z}(t)|$ of the beam forming output for the given time slot $t=t_1, t_1+1, \ldots, t_2$; $\{w(\omega)\}_\omega$ is a beam-forming weight coefficient; $\omega$ ($\omega=1, 2, \ldots, \Omega$) represents a band.

Embodiment 16: The beam forming method according to Embodiment 15, wherein based on an optimized linear transformation coefficient $\{g_i^*(\tau)\}$, according to the at least one EEG signal, the reconstructed envelope $\hat{s}_a(t)=\Sigma_i\Sigma_\tau g_i^*(\tau)e_i(t+\tau)$ of speech signals of attended speech sources is obtained, and the method further comprises receiving the reconstructed envelope of speech signals of attended speech sources, By solving the following formula, the optimized linear transformation coefficient $\{g_i^*(\tau)\}$ is obtained:

$$\min_{\{g_i(\tau)\}} \mathbb{E}\left\{\left\|\left[\sum_{i=1}^{C}\sum_{\tau=\tau_1}^{\tau_2} g_i(\tau)e_i(t+\tau)\right] - s_\alpha(t)\right\|^2\right\} + \lambda h(\{g_i(\tau)\}). \quad (2)$$

where $e_i(t)\in R$ is an EEG signal corresponding to EEG channel i (i=1, 2, ..., C) in the at least one EEG signal at time t (t=1, 2, ...) and $\tau$ is a time delay; $S_\alpha(t)$ represents an envelope of speech signals of the attended speech sources corresponding to the plurality of input signals; $g_i(\tau)$ is a linear regression coefficient of the EEG signal corresponding to EEG channel i with a delay $\tau$, and E is an expected operator; regular function $$h(\{g_i(\tau)\}) \triangleq \left[\sum_{i=1}^{C}\sum_{\tau=\tau_1}^{\tau_2-1} |g_i(\tau) - g_i(\tau+1)|^2 + \sum_{i=1}^{C}|g_i(\tau_2) - g_{i+1}(\tau_1)|^2\right]$$

delimits the time smoothness of the linear regression coefficient $g_i(\tau)$; and $\lambda \geq 0$ is a corresponding regular parameter.

Embodiment 17: The beam forming method according to Embodiment 16, wherein the analytical signal is expressed as follows through discrete Fourier transform (DFT) according to the beam-forming weight coefficient $\{w(\omega)\}_\Omega$:

$$\begin{bmatrix} \tilde{z}(t) \\ \tilde{z}(t+1) \\ \vdots \\ \tilde{z}(t+N-1) \end{bmatrix} = D_W F D_H \begin{bmatrix} w(1)^H y(\ell, 1) \\ w(2)^H y(\ell, 2) \\ \vdots \\ w(\Omega)^H y(\ell, \Omega) \end{bmatrix} \quad (3)$$

where $D_H \in R^{\Omega\times\Omega}$ is a diagonal matrix for forming the analytical signals and $F \in C^{\Omega\times\Omega}$ is the inverse of the DFT matrix; $y(l, \omega) \in C^M$ represents the plurality of input signals at frame/and band $\omega$ ($\omega=1, 2, \ldots, \Omega$), frame l corresponds to N sampling time points t, t+1, ..., t+N-1, while $D_W \in R^{\Omega\times\Omega}$ is a diagonal matrix for compensating a synthesis window used in short-time Fourier transform (STFT) that is used to express the plurality of input signals, and the analytical signal is further equivalently expressed as:

$$\tilde{z}(t+n)=w^H u_{\ell,n}, n=0,1,\ldots,N-1, \quad (4)$$

where $w=[w(1)^H, w(2)^H, \ldots, w(\Omega)^H]^H \in C^{M\Omega}$ is the beam-forming weight coefficient, and $u_{\ell,n} \in C^{M\Omega}$ is determined by $\{y(l\omega)\}_\omega$ and the coefficients in matrices $D_W$, F and $D_H$, and through the analytical signal, the envelope $|\tilde{z}(t)|$ of the beam forming output is expressed as:

$$|\tilde{z}(t+n)|=|w^H u_{\ell,n}|, n=0,1,\ldots,N-1. \quad (5).$$

Embodiment 18: The beam forming method according to Embodiment 17, wherein the sampling rate of the envelope $|\tilde{z}(t)|$ of the beam forming output corresponds to the audio sampling rate of the plurality of input signals.

Embodiment 19: The beam forming method according to Embodiment 17, wherein optimizing the association to construct a beam-forming weight coefficient associated with at least one electroencephalogram signal includes maximizing the Pearson correlation coefficient $\kappa(\{w(\omega)\})$ to extract the AA information contained in the at least one EEG signal.

Embodiment 20: The beam forming method according to Embodiment 19, wherein in the process of maximizing the Pearson correlation coefficient $\kappa(\{w(\omega)\})$, robust equality constraint $w(\omega)^H h_k(\omega)=\alpha_k, \forall\omega$ is applied to control speech distortion, where $\alpha=[\alpha_1, \alpha_2, \ldots, \alpha_K]^T$ is an additional variable, which represents AA preference in the plurality of speech sources; $h_k(\omega)$ is an acoustic transfer function of the k-th speech source; and K is the number of the plurality of speech sources.

Embodiment 21: The beam forming method according to Embodiment 20, wherein the optimization formula becomes:

$$\min_{\{w(\omega)\},\alpha} \sum_{\omega=1}^{\Omega} w(\omega)^H R_n(\omega) w(\omega) - \mu\kappa(\{w(\omega)\}) - \gamma\|\alpha\|^2 \quad (9)$$

$$\text{s.t. } w(\omega)^H h_k(\omega) = \alpha_k, \forall k, \omega,$$

$$1^T\alpha = 1, \alpha_k \geq 0, \forall k.$$

where $R_n(\omega) \triangleq \mathbb{E}[n(\omega)n(\omega)]$ is a correlation matrix of background noise; $-\gamma\|\alpha\|^2$ is a regular term of the optimization formula, where $\|\cdot\|^2$ represents a Euclidean norm of the additional variable $\alpha=[\alpha_1, \alpha_2, \ldots, \alpha_K]^T$; $\mu>$ and $\gamma\geq0$ are preset parameters and are used to balance denoising, allocate attention preferences and control the sparseness of attention preferences, and $1^T\alpha=1$, $\alpha_k\geq0$, $\forall k$ indicates that the sum of the elements in the additional variable is 1.

Embodiment 22: The beam forming method according to Embodiment 21, wherein the optimization model is solved by the gradient projection method (GPM) and the alternating direction method of multipliers (ADMM), including the following steps:

(a) The objective function in the optimization formula is expressed as:

$$f(\{w(\omega)\}, \alpha) \triangleq \sum_{\omega=1}^{\Omega} w(\omega)^H R_n(\omega) w(\omega) - \mu\kappa(\{w(\omega)\}) - \gamma\|\alpha\|^2,$$

and let $\nabla f = [\nabla f_1, \nabla f_2, \ldots, \nabla f_\Omega, \nabla f_\alpha]^T$ represent the gradient of the optimization formula, where $\nabla f_\omega$ represents a gradient component about $w(\omega)$; and $\nabla f_\alpha$ represents a gradient component about $\alpha$;

(b) The GPM iteratively updates $x \triangleq (\{w(\omega)\}, \alpha)$ to:

$$\bar{x} = [x^t - s\nabla f^t]^+ \quad (10a)$$

$$x^{t+1} = x^t + \lambda^t(\bar{x} - x^t), \quad (10b)$$

where t is an iteration index, $\nabla f^t$ is a gradient of the objective function at $x^t$, $[\cdot]^+$ represents projection operation of equality constraints $w(\omega)^H h_k(\omega) = \alpha_k$, $\forall \omega$ and $1^T\alpha=1$, $\alpha_k \geq 0$, $\forall k$, is a constant, and $\lambda^t$ is a step size determined according to the Armijo rule;

(c) The projection operation in Formula (10a) is same as the following convex optimization equation:

$$\min_{\{w(\omega)\},\alpha} \sum_{\omega=1}^{\Omega} \|w(\omega) - s\nabla f_\omega\|^2 + \|\alpha - s\nabla f_\alpha\|^2 \quad (11a)$$

$$\text{s.t. } w(\omega)^H h_k(\omega) = \alpha_k, \forall k, \omega, \quad (11b)$$

$$1^T\alpha = 1, \alpha_k \geq 0, \forall k. \quad (11c)$$

The augmented Lagrangian function for Equations 11a, 11b and 11c is:

$$L_\rho(\{w(\omega)\}, \alpha, \{\zeta_{k,\omega}\}, \eta) = \sum_{\omega=1}^{\Omega} \|w(\omega) - s\nabla f_\omega\|^2 + \|\alpha - s\nabla f_\alpha\|^2 + \eta(\alpha - 1) +$$

$$\frac{\rho}{2}\|1^T\alpha - 1\|^2 + \sum_{k=1}^{K}\sum_{\omega=1}^{\Omega} \zeta_{k,\omega}[w(\omega)^H h_k(\omega) - \alpha_k] + \frac{\rho}{2}\|w(\omega)^H h_k(\omega) - \alpha_k\|^2,$$

where $\zeta_{k,w}$ and $\eta$ are Lagrangian factors, which are correlated to the equality constraints; $\rho>0$ is a predefined parameter for the ADMM algorithm, (d) The ADMM algorithm iteratively updates $(\{w(\omega)\}, \alpha, \{\zeta_{k,\omega}\}, \eta)$ into:

$$w^{l+1}(\omega') = \arg\min_{w(\omega')} L_\rho(w(\omega'), \{w^l(\omega)\}_{\omega \neq \omega'}, \alpha^l, \{\zeta_{k,\omega}^l\}, \eta^l), \forall \omega' \quad (12a)$$

$$\alpha = \arg\min_{\alpha \geq 0} L_\rho(\{\omega^{l+1}(\omega)\}, \alpha, \{\zeta_{k,\omega}^l\}, \eta^l) \quad (12b)$$

$$\zeta_{k,\omega}^{l+1} = \zeta_{k,\omega}^l + \rho[\omega^{l+1}(\omega)^H h_k(\omega) - \alpha_k^{l+1}], \forall k, \omega \quad (12c)$$

$$\eta^{l+1} = \eta^l + \rho(1^T\alpha - 1) \quad (12d)$$

where l is an iteration index; and (e) A result of Formula 12 is obtained.

Embodiment 23: An ear-mounted hearing system, comprising:

a microphone, which is configured to receive a plurality of input signals from a plurality of speech sources;

an electroencephalogram signal receiving interface, which is configured to receive information from one or more electroencephalogram electrodes and perform linear or non-linear transformation on the electroencephalogram information to form at least one electroencephalogram (EEG) signal;

a beam former, which receives the plurality of input signals and the at least one EEG signal and outputs a beam-forming weight coefficient; and a synthesis module, which linearly or non-linearly synthesizes the plurality of input signals and the beam-forming weight coefficient to form a beam forming output, and a loudspeaker, which is configured to convert the beam forming output into an output sound, wherein the beam former is a beam former according to any of Embodiments 1 to 11.

Embodiment 24: A computer-readable medium including instructions, wherein when being executed by a processor, the instructions can cause the processor to implement the beam forming method according to any of Embodiments 12 to 22.

The present application is designed to cover the implementation manners or variants of the subject matter of the present application. It should be understood that the description is exemplary rather than restrictive.

The invention claimed is:

1. A beam former, comprising:
   a linear transformation module for receiving at least one electroencephalogram (EEG) signal and a plurality of input signals from a plurality of speech sources; and
   an electroencephalogram beam former for constructing an optimization model and solving the optimization model to obtain a beam-forming weight coefficient for performing linear or non-linear combination on the plurality of input signals;
   wherein the optimization model comprises an optimization formula for obtaining the beam-forming weight coefficient, and the optimization formula comprises establishing an association between the at least one electroencephalogram signal and a beam forming output, and optimizing the association to construct a beam-forming weight coefficient associated with at least one electroencephalogram signal.

2. The beam former according to claim 1, wherein establishing an association between the at least one electroencephalogram signal and a beam forming output includes establishing an association between the at least one electroencephalogram signal and a beam forming output by using non-linear transformation or by a method using a neural network.

3. The beam former according to claim 1, wherein establishing an association between the at least one electroencephalogram signal and a beam forming output includes using linear transformation to establish an association between the at least one electroencephalogram signal and a beam forming output.

4. The beam former according to claim 3, wherein the optimization formula comprises a Pearson correlation coefficient:

$$\kappa(\{w(\omega)\}) = \frac{\sum_{t=t_1}^{t_2} \psi_{s,t} \psi_{z,t}(\{w(\omega)\})}{\sqrt{\frac{1}{t_2-t_1+1}\sum_{t=t_1}^{t_2} \psi_{s,t}^2} \sqrt{\frac{1}{t_2-t_1+1}\sum_{t=t_1}^{t_2} \psi_{z,t}(\{w(\omega)\})^2}}, \quad (6)$$

where $$\psi_{s,t} = \hat{s}_a(t) - \frac{1}{t_s - t_1 + 1}\sum_{t'=t_1}^{t_2} \hat{s}_a(t'),$$

$$\psi_{z,t}(\{w(\omega)\}) = |\tilde{z}(t)| - \frac{1}{t_2-t_1+1}\sum_{t'=t_1}^{t_2} |\tilde{z}(t')|,$$

and where $\hat{s}_a(t)$ is an envelope of speech signals of attended speech sources, which is reconstructed by the at least one EEG signal; z(t) represents a beam forming output; $\tilde{z}(t)$ is an analytical signal corresponding to the beam forming output; $|\tilde{z}(t)|$ is an envelope of the beam forming output and is an absolute value of the analytical signal $\tilde{z}(t)$; $\kappa(\{w(\omega)\})$ represents the Pearson correlation coefficient between the reconstructed envelope $\hat{s}_a(t)$ of speech signals of attended speech sources and the envelope $|\tilde{z}(t)|$ of the beam forming output for the given time slots $t=t_1, t_1+1, \ldots, t_2$; $\{w(\omega)\}_\omega$ is the beam-forming weight coefficient; $\omega$ ($\omega=1, 2, \ldots, \Omega$) represents a band.

5. The beam former according to claim 4, further comprising a device for receiving a reconstructed envelope of speech signals of attended speech sources, wherein based on an optimized linear transformation coefficient $\{g_i^*(\tau)\}$, according to the at least one EEG signal, the reconstructed envelope $\hat{s}_a(t) = \Sigma_i \Sigma_\tau g_i^*(\tau) e_i(t+\tau)$ of speech signals of attended speech sources is obtained, and the reconstructed envelope of speech signals of attended speech sources is transferred to the device for receiving a reconstructed envelope of speech signals of attended speech sources, wherein by solving the following formula, the optimized linear transformation coefficient $\{g_i^*(\tau)\}$ is obtained:

$$\min_{\{g_i(\tau)\}} \mathbb{E}\left\{\left\|\left[\sum_{i=1}^{C}\sum_{\tau=\tau_1}^{\tau_2} g_i(\tau)e_i(t+\tau)\right] - s_\alpha(t)\right\|^2\right\} + \lambda h(\{g_i(\tau)\}). \quad (2)$$

where $e_i(t) \in R$ is an EEG signal corresponding to EEG channel i (i=1, 2, ..., C) in the at least one EEG signal at time t (t=1, 2, ... ) and z is a time delay; $S_\alpha(t)$ represents an envelope of speech signals of the attended speech sources corresponding to the plurality of input signals; $g_i(\tau)$ is a linear regression coefficient of the EEG signal corresponding to the EEG channel i with a delay τ, and E is an expected operator; regular function $$h(\{g_i(\tau)\}) \triangleq \left[\sum_{i=1}^{C}\sum_{\tau=\tau_1}^{\tau_2-1} |g_i(\tau) - g_i(\tau+1)|^2 + \sum_{i=1}^{C}|g_i(\tau_2) - g_{i+1}(\tau_1)|^2\right]$$

delimits the time smoothness of the linear regression coefficient $g_i(\tau)$; and $\lambda \geq 0$ is a corresponding regular parameter.

6. The beam former according to claim 5, wherein the analytical signal is expressed as follows through discrete Fourier transform (DFT) according to the beam-forming weight coefficient $\{w(\omega)\}_\omega$:

$$\begin{bmatrix} \tilde{z}(t) \\ \tilde{z}(t+1) \\ \vdots \\ \tilde{z}(t+N-1) \end{bmatrix} = D_W F D_H \begin{bmatrix} w(1)^H y(\ell, 1) \\ w(2)^H y(\ell, 2) \\ \vdots \\ w(\Omega)^H y(\ell, \Omega) \end{bmatrix} \quad (3)$$

where $D_H \in R^{\Omega \times \Omega}$ is a diagonal matrix for forming the analytical signals and $F \in C^{\Omega \times \Omega}$ is the inverse of the DFT matrix; y(l, ω) ∈ $C^M$ represents the plurality of input signals at frame l and band ω (ω=1, 2, ..., Ω), frame l corresponds to N sampling time points t, t+1, ..., t+N−1, while $D_W \in R^{\Omega \times \Omega}$ is a diagonal matrix for compensating a synthesis window used in short-time Fourier transform (STFT) that is used to express the plurality of input signals, and
the analytical signal is further equivalently expressed as:

$$\tilde{z}(t+n) = w^H u_{\ell,n}, n=0,1,\ldots,N-1, \quad (4)$$

where $w=[w(1)^H, w(2)^H, \ldots, w(\Omega)^H]^H \in \mathbb{C}^{M\Omega}$ is the beam-forming weight coefficient, and $u_{l,n} \in \mathbb{C}^{M\Omega}$ is determined by $\{y(l\omega)\}_\omega$ and the coefficients in matrices $D_W$, F and $D_H$, and
through the analytical signals, the envelope $|\tilde{z}(t)|$ of the beam forming output is expressed as:

$$|\tilde{z}(t+n)| = |w^H u_{\ell,n}|, n=0,1,\ldots,N-1. \quad (5)$$

7. The beam former according to claim 6, wherein the sampling rate of the envelope $|\tilde{z}(t)|$ of the beam forming output corresponds to the audio sampling rate of the plurality of input signals.

8. The beam former according to claim 6, wherein optimizing the association to construct a beam-forming weight coefficient associated with at least one electroencephalogram signal includes maximizing the Pearson correlation coefficient $\kappa(\{w(\omega)\})$ to extract the AA information contained in the at least one EEG signal.

9. The beam former according to claim 8, wherein in the process of maximizing the Pearson correlation coefficient $\kappa(\{w(\omega)\})$, robust equality constraint $w(\omega)^H h_k(\omega) = \alpha_k$, $\forall \omega$ is applied to control speech distortion,
where $\alpha = [\alpha_1, \alpha_2, \ldots, \alpha_K]^T$ is an additional variable, which represents AA preference in the plurality of speech sources; $h_k(\omega)$ is an acoustic transfer function of the k-th speech source; and K is the number of the plurality of speech sources.

10. The beam former according to claim 9, wherein the optimization formula becomes:

$$\min_{\{w(\omega)\},\alpha} \sum_{\omega=1}^{\Omega} w(\omega)^H R_n(\omega) w(\omega) - \mu \kappa(\{w(\omega)\}) - \gamma \|\alpha\|^2 \quad (9)$$

s.t. $w(\omega)^H h_k(\omega) = \alpha_k, \forall k, \omega,$ $1^T \alpha = 1, \alpha_k \geq 0, \forall k.$ where $R_n(\omega) \triangleq \mathbb{E}[n(\omega)n(\omega)]$ is a correlation matrix of background noise; $-\gamma\|\alpha\|^2$ is a regular term of the optimization formula, where $\|\cdot\|^2$ represents a Euclidean norm of the additional variable $\alpha=[\alpha_1, \alpha_2, \ldots, \alpha_K]^T$; $\mu>$ and $\gamma\geq 0$ are preset parameters and are used to balance denoising, allocate attention preferences and control the sparseness of attention preferences, and $1^T\alpha=1, \alpha_k\geq 0, \forall k$ indicates that the sum of the elements in the additional variable is 1.

11. The beam former according to claim 10, wherein the optimization model is solved by the gradient projection method (GPM) and the alternating direction method of multipliers (ADMM), including the following steps:
(a) The objective function in the optimization formula is expressed as:

$$f(\{w(\omega)\}, \alpha) \triangleq \sum_{\omega=1}^{\Omega} w(\omega)^H R_n(\omega) w(\omega) - \mu \kappa(\{w(\omega)\}) - \gamma \|\alpha\|^2$$

and let $\nabla f = [\nabla f_1, \nabla f_2, \ldots, \nabla f_\Omega, \nabla f_\alpha]^T$ represent the gradient of the optimization formula,
where $\nabla f_\omega$ represents a gradient component about $w(\omega)$; and $\nabla f_\alpha$ represents a gradient component about $\alpha$;
(b) The GPM iteratively updates $x \triangleq (\{w(\omega)\}, \alpha)$ to:

$$\bar{x} = [x^t - s\nabla f^t]^+ \quad (10a)$$

$$x^{t+1} = x^t + \lambda^t(\bar{x} - x^t), \quad (10b)$$

where t is an iteration index, $\nabla f^t$ of is a gradient of the objective function at $x^t$, $[\cdot]^+$ represents the projection operation of equality constraints $w(\omega)^H h_k(\omega)=\alpha_k, \forall \omega$ and $1^T\alpha=1, \alpha_k\geq 0, \forall k$, s is a constant, and $\lambda^t$ is a step size determined according to the Armijo rule;
(c) The projection operation in Formula (10a) is same as the following convex optimization equation:

$$\min_{\{w(\omega)\},\alpha} \sum_{\omega=1}^{\Omega} \|w(\omega) - s\nabla f_\omega\|^2 + \|\alpha - s\nabla f_\alpha\|^2 \quad (11a)$$

s.t. $w(\omega)^H h_k(\omega) = \alpha_k, \forall k, \omega,$ (11b)

$1^T \alpha = 1, \alpha_k \geq 0, \forall k.$ (11c)

The augmented Lagrangian function for Equations 11a, 11b and 11c is:

$$L_\rho(\{w(\omega)\}, \alpha, \{\zeta_{k,\omega}\}, \eta) = \sum_{\omega=1}^{\Omega} \|w(\omega) - s\nabla f_\omega\|^2 + \|\alpha - s\nabla f_\alpha\|^2 + \eta(\alpha - 1) +$$

$$\frac{\rho}{2}\|1^T\alpha - 1\|^2 + \sum_{k=1}^{K}\sum_{\omega=1}^{\Omega} \zeta_{k,\omega}[w(\omega)^H h_k(\omega) - \alpha_k] + \frac{\rho}{2}\|w(\omega)^H h_k(\omega) - \alpha_k\|^2,$$

where $\zeta_{k,w}$ and $\eta$ are Lagrangian factors, which are correlated to the equality constraints respectively; $\rho>0$ is a predefined parameter for the ADMM algorithm,
(d) The ADMM algorithm iteratively updates ($\{w(\omega)\}$, $\alpha$, $\{\zeta_{k,w}\}$, $\eta$) into:

$$w^{l+1}(\omega') = \underset{w(\omega')}{\arg\min} L_\rho(w(\omega'), \{w^l(\omega)\}_{\omega\neq\omega'}, \alpha^l, \{\zeta^l_{k,\omega}\}, \eta^l), \forall \omega' \quad (12a)$$

$$\alpha = \underset{\alpha\geq 0}{\arg\min} L_\rho(\{\omega^{l+1}(\omega)\}, \alpha, \{\zeta^l_{k,\omega}\}, \eta^l) \quad (12b)$$

$$\zeta^{l+1}_{k,\omega} = \zeta^l_{k,\omega} + \rho[\omega^{l+1}(\omega)^H h_k(\omega) - \alpha^{l+1}_k], \forall k, \omega \quad (12c)$$

$$\eta^{l+1} = \eta^l + \rho(1^T\alpha - 1) \quad (12d)$$

where l is an iteration index; and
(e) A result of Formula 12 is obtained.

12. An ear-mounted hearing system, comprising: a microphone, which is configured to receive a plurality of input signals from a plurality of speech sources; an electroencephalogram signal receiving interface, which is configured to receive information from one or more electroencephalogram electrodes and perform linear or non-linear transformation on the electroencephalogram information to form at least one electroencephalogram (EEG) signal; a beam former, which receives the plurality of input signals and the at least one EEG signal and outputs a beam-forming weight coefficient; and a synthesis module, which linearly or non-linearly synthesizes the plurality of input signals and the beam-forming weight coefficient to form a beam forming output, and a loudspeaker, which is configured to convert the beam forming output into an output sound, wherein the beam former is a beam former according to claim 1.

13. A beam forming method for beam former, comprising the following steps:
receiving at least one electroencephalogram (EEG) signal and a plurality of input signals from a plurality of speech sources; and
constructing an optimization model and solving the optimization model to obtain a beam-forming weight coefficient for performing linear or non-linear combination on the plurality of input signals;
wherein the optimization model comprises an optimization formula for obtaining the beam-forming weight coefficient, and the optimization formula comprises establishing an association between the at least one electroencephalogram signal and a beam forming output, and optimizing the association to construct a beam-forming weight coefficient associated with at least one electroencephalogram signal.

14. The beam forming method according to claim 13, wherein establishing an association between the at least one electroencephalogram signal and a beam forming output includes establishing an association between the at least one electroencephalogram signal and a beam forming output by using nonlinear transformation or by a method using a neural network.

15. The beam forming method according to claim 13, wherein establishing an association between the at least one electroencephalogram signal and a beam forming output includes establishing an association between the at least one electroencephalogram signal and a beam forming output by using linear transformation.

16. The beam forming method according to claim 15, wherein the optimization formula includes a Pearson correlation coefficient:

$$\kappa(\{w(\omega)\}) = \frac{\sum_{t=t_1}^{t_2} \psi_{s,t}\psi_{z,t}(\{w(\omega)\})}{\sqrt{\frac{1}{t_2-t_1+1}\sum_{t=t_1}^{t_2}\psi_{s,t}^2}\sqrt{\frac{1}{t_2-t_1+1}\sum_{t=t_1}^{t_2}\psi_{z,t}(\{w(\omega)\})^2}}, \quad (6)$$

where $$\psi_{s,t} = \hat{s}_a(t) - \frac{1}{t_s-t_1+1}\sum_{t'=t_1}^{t_2}\hat{s}_a(t'),$$

$$\psi_{z,t}(\{w(\omega)\}) = |\tilde{z}(t)| - \frac{1}{t_2-t_1+1}\sum_{t'=t_1}^{t_2}|\tilde{z}(t')|$$

and where $\hat{s}_a(t)$ is an envelope of speech signals of attended speech sources, which is reconstructed by the at least one EEG signal; z(t) represents a beam forming output; $\tilde{z}(t)$ is an analytical signal corresponding to the beam forming output; $|\tilde{z}(t)|$ is an envelope of the beam forming output and is an absolute value of the analytical signal $\tilde{z}(t)$; $\kappa(\{w(\omega)\})$ represents a Pearson correlation coefficient between the reconstructed envelope $\hat{s}_a(t)$ of speech signals of speech sources and the envelope $|\tilde{z}(t)|$ of the beam forming output for the given time slot $t=t_1, t_1+1, \ldots, t_2$; $\{w(\omega)\}_\omega$ is a beam-forming weight coefficient; $\omega$ ($\omega=1, 2, \ldots, \Omega$) represents a band.

17. The beam forming method according to claim 16, wherein based on an optimized linear transformation coefficient $\{g_i^*(\tau)\}$, according to the at least one EEG signal, the reconstructed envelope $\hat{s}_a(t)=\Sigma_i\Sigma_\tau g_i^*(\tau)e_i(t+\tau)$ of speech signals of attended speech sources is obtained, and the method further comprises receiving the reconstructed envelope of speech signals of attended speech sources, By solving the following formula, the optimized linear transformation coefficient $\{g_i^*(\tau)\}$ is obtained:

$$\min_{\{g_i(\tau)\}}\mathbb{E}\left\{\left\|\left[\sum_{i=1}^{C}\sum_{\tau=\tau_1}^{\tau_2}g_i(\tau)e_i(t+\tau)\right] - s_\alpha(t)\right\|^2\right\} + \lambda h(\{g_i(\tau)\}). \quad (2)$$

where $e_i(t)\in R$ is an EEG signal corresponding to EEG channel i (i=1, 2, ..., C) in the at least one EEG signal at time t (t=1, 2, ...) and $\tau$ is a time delay; $S_\alpha(t)$ represents an envelope of speech signals of the attended speech sources corresponding to the plurality of input signals; $g_i(\tau)$ is a linear regression coefficient of the EEG signal corresponding to EEG channel i with a delay $\tau$, and E is an expected operator; regular function $$h(\{g_i(\tau)\}) \triangleq \left[\sum_{i=1}^{C}\sum_{\tau=\tau_1}^{\tau_2-1}|g_i(\tau) - g_i(\tau+1)|^2 + \sum_{i=1}^{C-1}|g_i(\tau_2) - g_{i+1}(\tau_1)|^2\right]$$

delimits the time smoothness of the linear regression coefficient $g_i(\tau)$; and $\lambda\geq 0$ is a corresponding regular parameter.

18. The beam forming method according to claim 17, wherein the analytical signal is expressed as follows through discrete Fourier transform (DFT) according to the beam-forming weight coefficient $\{w(\omega)\}_\omega$:

$$\begin{bmatrix} \tilde{z}(t) \\ \tilde{z}(t+1) \\ \vdots \\ \tilde{z}(t+N-1) \end{bmatrix} = D_W F D_H \begin{bmatrix} w(1)^H y(\ell, 1) \\ w(2)^H y(\ell, 2) \\ \vdots \\ w(\Omega)^H y(\ell, \Omega) \end{bmatrix} \quad (3)$$

where $D_H \in R^{\Omega\times\Omega}$ is a diagonal matrix for forming the analytical signals and $F\in C^{\Omega\times\Omega}$ is the inverse of the DFT matrix; y(l, $\omega)\in C^M$ represents the plurality of input signals at frame l and band $\omega$ ($\omega=1, 2, \ldots, \Omega$), frame l corresponds to N sampling time points t+1, ..., t+N−1, while $D_W\in R^{\Omega\times\Omega}$ is a diagonal matrix for compensating a synthesis window used in short-time Fourier transform (STFT) that is used to express the plurality of input signals, and the analytical signal is further equivalently expressed as:

$$\tilde{z}(t+n) = w^H u_{\ell,n}, n=0,1,\ldots,N-1, \quad (4)$$

where $w=[w(1)^H, w(2)^H, \ldots, w(\Omega)^H]^H \in \mathbb{C}^{M\Omega}$ is the beam-forming weight coefficient, and $u_{l,n}\in \mathbb{C}^{M\Omega}$ is determined by $\{y(l\omega)\}_\omega$ and the coefficients in matrices $D_W$, F and $D_H$, and through the analytical signal, the envelope $|\tilde{z}(t)|$ of the beam forming output is expressed as:

$$|\tilde{z}(t+n)| = |w^H u_{\ell,n}|, n=0,1,\ldots,N-1. \quad (5)$$

19. The beam forming method according to claim 18, wherein the sampling rate of the envelope $|\tilde{z}(t)|$ of the beam forming output corresponds to the audio sampling rate of the plurality of input signals.

20. The beam forming method according to claim 18, wherein optimizing the association to construct a beam-forming weight coefficient associated with at least one electroencephalogram signal includes maximizing the Pearson correlation coefficient $\kappa(\{w(\omega)\})$ to extract the AA information contained in the at least one EEG signal.

21. The beam forming method according to claim 20, wherein in the process of maximizing the Pearson correlation coefficient $\kappa(\{w(\omega)\})$, robust equality constraint $w(\omega)^H h_k(\omega)=\alpha_k$, $\forall\omega$ is applied to control speech distortion, where $\alpha=[\alpha_1, \alpha_2, \ldots, \alpha_K]^T$ is an additional variable, which represents AA preference in the plurality of speech sources; $h_k(\omega)$ is an acoustic transfer function of the k-th speech source; and K is the number of the plurality of speech sources.

22. The beam forming method according to claim 21, wherein the optimization formula becomes:

$$\min_{\{w(\omega)\},\alpha}\sum_{\omega=1}^{\Omega} w(\omega)^H R_n(\omega)w(\omega) - \mu\kappa(\{w(\omega)\}) - \gamma\|\alpha\|^2 \quad (9)$$

$$\text{s.t. } w(\omega)^H h_k(\omega) = \alpha_k, \forall k, \omega,$$

$$1^T\alpha = 1, \alpha_k \geq 0, \forall k.$$

where $R_n(\omega) \triangleq \mathbb{E}[n(\omega)n(\omega)]$ is a correlation matrix of background noise; $-\gamma\|\alpha\|^2$ is a regular term of the optimization formula, where $\|\cdot\|^2$ represents a Euclidean norm of the additional variable $\alpha=[\alpha_1, \alpha_2, \ldots, \alpha_K]^T$; $\mu>$ and $\gamma\geq 0$ are preset parameters and are used to balance denoising, allocate attention preferences, and control the sparseness of attention preferences, and $1^T\alpha=1$, $\alpha_k\geq 0$, $\forall k$ indicates that the sum of the elements in the additional variable is 1.

23. The beam forming method according to claim 22, wherein the optimization model is solved by the gradient projection method (GPM) and the alternating direction method of multipliers (ADMM), including the following steps:

(a) The objective function in the optimization formula is expressed as:

$$f(\{w(\omega)\}, \alpha) \triangleq \sum_{\omega=1}^{\Omega} w(\omega)^H R_n(\omega) w(\omega) - \mu \kappa(\{w(\omega)\}) - \gamma \|\alpha\|^2,$$

and let $\nabla f = [\nabla f_1, \nabla f_2, \ldots, \nabla f_\Omega, \nabla f_\alpha]^T$ represent the gradient of the optimization formula, where $\nabla f_\omega$ represents a gradient component about $w(\omega)$; and $\nabla f_\alpha$ represents a gradient component about $\alpha$;

(b) The GPM iteratively updates $x \triangleq (\{w(\omega)\}, \alpha)$ to:

$$\bar{x} = [x^t - s\nabla f^t]^+ \quad (10a)$$

$$x^{t+1} = x^t + \lambda^t (\bar{x} - x^t), \quad (10b)$$

where t is an iteration index, $\nabla f^t$ of is a gradient of the objective function at $x^t$, $[\cdot]^+$ represents projection operation of equality constraints $w(\omega)^H h_k(\omega) = \alpha_k$, $\forall \omega$ and $1^T\alpha = 1$, $\alpha_k \geq 0$, $\forall k$, s is a constant, and $\lambda^t$ is a step size determined according to the Armijo rule;

(c) The projection operation in Formula (10a) is same as the following convex optimization equation:

$$\min_{\{w(\omega)\}, \alpha} \sum_{\omega=1}^{\Omega} \|w(\omega) - s\nabla f_\omega\|^2 + \|\alpha - s\nabla f_\alpha\|^2 \quad (11a)$$

$$\text{s.t. } w(\omega)^H h_k(\omega) = \alpha_k, \forall k, \omega, \quad (11b)$$

$$1^T\alpha = 1, \alpha_k \geq 0, \forall k. \quad (11c)$$

The augmented Lagrangian function for Equations 11a, 11b and 11c is:

$$L_\rho(\{w(\omega)\}, \alpha, \{\zeta_{k,\omega}\}, \eta) = \sum_{\omega=1}^{\Omega} \|w(\omega) - s\nabla f_\omega\|^2 + \|\alpha - s\nabla f_\alpha\|^2 + \eta(\alpha - 1) +$$

$$\frac{\rho}{2}\|1^T\alpha - 1\|^2 + \sum_{k=1}^{K}\sum_{\omega=1}^{\Omega} \zeta_{k,\omega}\left[w(\omega)^H h_k(\omega) - \alpha_k\right] + \frac{\rho}{2}\|w(\omega)^H h_k(\omega) - \alpha_k\|^2,$$

where $\zeta_{k,w}$ and $\eta$ are Lagrangian factors, which are correlated to the equality constraints; $\rho > 0$ is a predefined parameter for the ADMM algorithm, (d) The ADMM algorithm iteratively updates ($\{w(\omega)\}$, $\alpha$, $\{\zeta_{k,\omega}\}$, $\eta$) into:

$$w^{l+1}(\omega') = \underset{w(\omega')}{\arg\min} L_\rho\left(w(\omega'), \{w^l(\omega)\}_{\omega \neq \omega'}, \alpha^l, \{\zeta_{k,\omega}^l\}, \eta^l\right), \forall \omega' \quad (12a)$$

$$\alpha = \underset{\alpha \geq 0}{\arg\min} L_\rho\left(\{\omega^{l+1}(\omega)\}, \alpha, \{\zeta_{k,\omega}^l\}, \eta^l\right) \quad (12b)$$

$$\zeta_{k,\omega}^{l+1} = \zeta_{k,\omega}^l + \rho\left[\omega^{l+1}(\omega)^H h_k(\omega) - \alpha_k^{l+1}\right], \forall k, \omega \quad (12c)$$

$$\eta^{l+1} = \eta^l + \rho(1^T\alpha - 1) \quad (12d)$$

where l is an iteration index; and (e) A result of Formula 12 is obtained.

24. A non-transitory computer-readable medium including instructions, wherein when being executed by a processor, the instructions can cause the processor to implement the beam forming method according to claim 13.

\* \* \* \* \*